US009933348B2

(12) United States Patent
Esteves Reis et al.

(10) Patent No.: US 9,933,348 B2
(45) Date of Patent: Apr. 3, 2018

(54) SEQUENTIAL ALIQOTING AND DETERMINATION OF AN INDICATOR OF SEDIMENTATION RATE

(71) Applicant: BIOSURFIT S.A., Aveiro (PT)

(72) Inventors: Nuno Alexandre Esteves Reis, Sintra (PT); Joao Manuel De Oliveira Garcia Da Fonseca, Azambuja (PT)

(73) Assignee: Biosurfit, S.A., Aveiro (PT)

( * ) Notice: Subject to any disclaimer, the term of this patent is extended or adjusted under 35 U.S.C. 154(b) by 822 days.

(21) Appl. No.: 14/363,491

(22) PCT Filed: Dec. 7, 2012

(86) PCT No.: PCT/EP2012/074874
§ 371 (c)(1),
(2) Date: Jun. 6, 2014

(87) PCT Pub. No.: WO2013/083822
PCT Pub. Date: Jun. 13, 2013

(65) Prior Publication Data
US 2014/0352410 A1 Dec. 4, 2014

(30) Foreign Application Priority Data

Dec. 8, 2011 (PT) .................................. 106053
Dec. 8, 2011 (PT) .................................. 106054

(51) Int. Cl.
*G01N 37/00* (2006.01)
*G01N 15/05* (2006.01)
(Continued)

(52) U.S. Cl.
CPC .......... *G01N 15/05* (2013.01); *B01L 3/50273* (2013.01); *B01L 3/502723* (2013.01);
(Continued)

(58) Field of Classification Search
CPC ........................................................ G01N 15/05
(Continued)

(56) References Cited

U.S. PATENT DOCUMENTS 5,087,532 A 2/1992 Challener, IV
5,414,678 A 5/1995 Challener, IV
(Continued)

FOREIGN PATENT DOCUMENTS

DE 102005048233 4/2007
EP 0608006 7/1994
(Continued)

OTHER PUBLICATIONS

Office Action dated Oct. 18, 2016 for Japanese Application No. 2014-545300, 12 pages.
(Continued)

*Primary Examiner* — John Fitzgerald
*Assistant Examiner* — Rodney T Frank
(74) *Attorney, Agent, or Firm* — Patterson Thuente Pedersen, P.A.

(57) ABSTRACT

A device is disclosed for centrifugally driving liquid flow to sequentially dispense aliquots from a reservoir while the device rotates. Also disclosed is a method and system for analyzing a liquid to derive an indicator of sedimentation rate of the liquid using sequential aliquoting, using the disclosed device in some embodiments. A particular application is the analysis of blood samples, including sedimentation rate and hematocrit.

8 Claims, 23 Drawing Sheets

(51) Int. Cl.
| | |
|---|---|
| *B01L 3/00* | (2006.01) |
| *G01N 15/04* | (2006.01) |
| *G01N 35/00* | (2006.01) |
| *B04B 11/00* | (2006.01) |
| *B04B 15/08* | (2006.01) |
| *G01N 35/04* | (2006.01) |
| *G01N 35/10* | (2006.01) |
| *G01N 33/49* | (2006.01) |
| *G01N 15/00* | (2006.01) |

(52) U.S. Cl.
CPC ........ *B01L 3/502753* (2013.01); *B04B 11/00* (2013.01); *B04B 15/08* (2013.01); *G01N 15/042* (2013.01); *G01N 35/00069* (2013.01); *B01L 3/502738* (2013.01); *B01L 2200/0621* (2013.01); *B01L 2300/0803* (2013.01); *B01L 2300/0864* (2013.01); *B01L 2300/0883* (2013.01); *B01L 2400/0409* (2013.01); *B01L 2400/0694* (2013.01); *G01N 33/49* (2013.01); *G01N 2015/0065* (2013.01); *G01N 2015/055* (2013.01); *G01N 2035/00495* (2013.01); *G01N 2035/0443* (2013.01); *G01N 2035/0449* (2013.01); *G01N 2035/1032* (2013.01)

(58) Field of Classification Search
USPC ........................................................ 73/61.44
See application file for complete search history.

(56) References Cited

U.S. PATENT DOCUMENTS

| | | | |
|---|---|---|---|
| 5,508,982 | A | 4/1996 | Challener, IV |
| 5,620,792 | A | 4/1997 | Challener, IV |
| 5,639,567 | A | 6/1997 | Challener, IV |
| 5,751,482 | A | 5/1998 | Challener, IV |
| 5,925,878 | A | 7/1999 | Challener |
| 5,955,378 | A | 9/1999 | Challener |
| 5,986,762 | A | 11/1999 | Challener |
| 5,986,997 | A | 11/1999 | Challener, IV |
| 5,994,150 | A | 11/1999 | Challener et al. |
| 6,063,589 | A | 5/2000 | Kellogg et al. |
| 6,100,991 | A | 8/2000 | Challener |
| 6,230,991 | B1 | 5/2001 | Steinruck et al. |
| 6,235,531 | B1 | 5/2001 | Kopf-Sill et al. |
| 6,277,653 | B1 | 8/2001 | Challener et al. |
| 6,320,991 | B1 | 11/2001 | Challener et al. |
| RE37,473 | E | 12/2001 | Challener |
| 6,344,490 | B1 | 2/2002 | Degeorge et al. |
| 6,625,336 | B2 | 9/2003 | Challener et al. |
| 6,632,399 | B1 | 10/2003 | Kellogg et al. |
| 6,653,152 | B2 | 11/2003 | Challener |
| 6,944,101 | B2 | 9/2005 | Johns et al. |
| 6,944,112 | B2 | 9/2005 | Challener |
| 7,027,700 | B2 | 4/2006 | Challener |
| 7,106,935 | B2 | 9/2006 | Challener |
| 7,266,268 | B2 | 9/2007 | Challener et al. |
| 7,272,102 | B2 | 9/2007 | Challener |
| 7,275,858 | B2 | 10/2007 | Andersson et al. |
| 7,330,404 | B2 | 2/2008 | Peng et al. |
| 7,412,143 | B2 | 8/2008 | Rottmayer et al. |
| 7,440,660 | B1 | 10/2008 | Jin et al. |
| 7,480,214 | B2 | 1/2009 | Challener et al. |
| 7,515,372 | B2 | 4/2009 | Erden et al. |
| 7,580,602 | B2 | 8/2009 | Itagi et al. |
| 7,768,657 | B2 | 8/2010 | Jin et al. |
| 7,796,487 | B2 | 9/2010 | Chu et al. |
| 7,804,656 | B2 | 9/2010 | Gomez et al. |
| 7,830,775 | B2 | 11/2010 | Karns et al. |
| 7,869,162 | B2 | 1/2011 | Lu et al. |
| 7,869,309 | B2 | 1/2011 | Mihalcea et al. |
| 7,893,497 | B2 | 2/2011 | Takasu |
| 8,916,112 | B2 | 12/2014 | Garcia De Fonseca et al. |
| 2001/0031503 | A1 | 10/2001 | Challener et al. |
| 2002/0122364 | A1 | 9/2002 | Worthington et al. |
| 2003/0044322 | A1 | 3/2003 | Andersson et al. |
| 2003/0128633 | A1 | 7/2003 | Batra et al. |
| 2003/0137772 | A1 | 7/2003 | Challener |
| 2004/0039303 | A1 | 2/2004 | Wurster et al. |
| 2004/0053290 | A1 | 3/2004 | Terbrueggen et al. |
| 2004/0240327 | A1 | 12/2004 | Sendur et al. |
| 2005/0157597 | A1 | 7/2005 | Sendur et al. |
| 2005/0217741 | A1 | 10/2005 | Bohm |
| 2006/0144802 | A1 | 7/2006 | Kitawaki et al. |
| 2006/0186765 | A1 | 8/2006 | Hashimoto |
| 2006/0233061 | A1 | 10/2006 | Rausch et al. |
| 2007/0115787 | A1 | 5/2007 | Itagi et al. |
| 2007/0125942 | A1 | 6/2007 | Kido |
| 2007/0262034 | A1* | 11/2007 | Ducree ............ B01L 3/502746 210/788 |
| 2008/0019875 | A1 | 1/2008 | Shiga |
| 2008/0149190 | A1 | 6/2008 | Bedingham et al. |
| 2008/0170319 | A1 | 7/2008 | Seigler et al. |
| 2009/0120504 | A1 | 5/2009 | Andersson et al. |
| 2009/0207519 | A1 | 8/2009 | Erden et al. |
| 2009/0208171 | A1 | 8/2009 | Gage et al. |
| 2009/0246082 | A1 | 10/2009 | Saiki et al. |
| 2010/0097901 | A1 | 4/2010 | Challener et al. |
| 2010/0123965 | A1 | 5/2010 | Lee et al. |
| 2010/0307595 | A1 | 12/2010 | Mark et al. |
| 2011/0044147 | A1 | 2/2011 | Karns et al. |
| 2011/0290718 | A1 | 12/2011 | Garcia Da Fonseca et al. |
| 2012/0021447 | A1 | 1/2012 | Garcia Da Fonseca et al. |

FOREIGN PATENT DOCUMENTS

| | | |
|---|---|---|
| EP | 1900433 | 3/2008 |
| EP | 1955770 A2 | 8/2008 |
| EP | 2080554 | 7/2009 |
| FR | 2652416 A3 | 3/1991 |
| GB | 2479139 A | 10/2011 |
| GB | 2480130 A | 11/2011 |
| JP | 02-280084 | 11/1990 |
| JP | 2000514928 A | 11/2000 |
| JP | 2004117048 | 4/2004 |
| JP | 2007333716 A | 12/2007 |
| WO | WO95/33986 | 12/1995 |
| WO | WO9708556 | 3/1997 |
| WO | WO97/21090 | 6/1997 |
| WO | WO 98/53311 | 11/1998 |
| WO | WO0146465 | 6/2001 |
| WO | WO03060882 | 7/2003 |
| WO | WO2003064998 | 8/2003 |
| WO | WO2003102559 | 12/2003 |
| WO | WO2004003891 | 1/2004 |
| WO | WO2004003932 | 1/2004 |
| WO | WO2004032118 | 4/2004 |
| WO | WO2004107323 | 12/2004 |
| WO | WO2005045815 | 5/2005 |
| WO | WO 2006/038632 | 4/2006 |
| WO | WO 2006/038682 A1 | 4/2006 |
| WO | WO2007024829 | 3/2007 |
| WO | WO2007091097 | 8/2007 |
| WO | WO2008057000 | 5/2008 |
| WO | WO2008106782 | 9/2008 |
| WO | WO2010059736 | 5/2010 |
| WO | WO 2011/122972 A2 | 10/2011 |

OTHER PUBLICATIONS

International Search Report and Written Opinion for International Application No. PCT/EP2012/074874 dated Apr. 11, 2013.
International Report on Patentability for PCT/PT2009/000055 dated Apr. 26, 2011.
Japanese Notification for Refusal for Japanese Application No. 2012-545894 dispatch date Mar. 4, 2014.
Notification of Reasons for Refusal for Japanese Application No. 2011-543549, dispatch date May 7, 2013.
International Search Report for International Application No. PCT/PT2011/000009 dated Oct. 18, 2011.

(56) References Cited

OTHER PUBLICATIONS

International Search Report for International Application No. PCT/PT2009/000055 dated Apr. 7, 2010 and Great Britain Search Report for GB Application No. 0819508.3 dated Feb. 26, 2009.

Schomburg et al, "Microfluidic components in LIGA technique" J. Micromech. Microeng. vol. 4, pp. 186-191 (1994).

Ducree et al., "The Centrifugal microfluidic Bio-Disk platform," J. Micromech. Microeng. vol. 17, pp. S103-S115 (2007).

Furlan et al., "Behavior of microfludic amplifiers" Sensors and Actuators. vol. 51, pp. 239-246 (1996).

Furlan et al., "Comparison of Wall Attachment and Jet Deflection Microfluidic Amplifiers" Micro Electro Mechanical Systems, 1996, MEMS '96, Proceedings an Investigation of Micro Structures, Sensors, Actuators, Machines and Systems, IEEE The 9th Annual International Workshop. San Diego, CA pp. 372-377 (Feb. 11, 1996).

Grumann et al., "Batch-Mode Mixing on Certrifugal Microfluidic Platforms", Lab Chip. 2005. pp. 560-565. vol. 5.

Haeberle et al., "Certrifugal Micromixer", Chem. Eng. Technology. pp. 613-616. vol. 28, No. 5 (2005).

Sudarsan et al., "Multivortex Micromixing", Artie McFerrin Department of Chemical Engineering. vol. 103, No. 19. pp. 7228-7233.(2006).

Nguyen et al., "Micromixers—A Review", Institute of Physics Publishing. Journal of Micromechanics and Microengineering. vol. 15. pp. R1-R-16. (2005).

GB Combined Search and Examination Report for Application No. GB0823660.6 dated May 18, 2009.

GB Response to Search Report for Application No. GB0823660.6 dated Dec. 13, 2010.

International Search Report and Written Opinion for International Application No. PCT/PT2009/000081 dated May 10, 2010.

Fontana, "Theoretical and Experimental Study of the surface plasmon resonance effect on a recordable compact disk", Applied Optics. vol. 43, No. 7B pp. 79-87 Jan. 1, 2004.

Chiu et al., Calculation of Surface Plasmon Effect on Optical Discs, Jap. J. Appl. Phys. Part 1, vol. 43, No. 7B, pp. 4730-4735 (2004).

Application and File History for U.S. Appl. No. 13/125,777, filed Aug. 12, 2011, inventors João Garcia da Fonseca et al.

Application and File History for U.S. Appl. No. 13/143,070, filed Sep. 28, 2011, inventors João Garcia da Fonseca et al.

Application and File History for U.S. Appl. No. 13/518,639, filed Jun. 22, 2012, inventors João Garcia da Fonseca et al.

Application and File History for U.S. Appl. No. 13/638,378, filed Dec. 11, 2012, inventors João Garcia da Fonseca et al.

Search Report dated Feb. 2, 2012 for Portuguese Application No. 106054, 6 pages.

Search Report dated Feb. 6, 2012 for Portuguese Application No. 106053, 6 pages.

Shelat et al., "Differences in Erythrocyte Sedimentation Rates Using the Westergren Method and Centrifugation Method", American Society of Clinical Pathology. (2008).

Examination Report dated Jun. 29, 2017 for EP Application No. 12808733.5, 14 pages.

\* cited by examiner

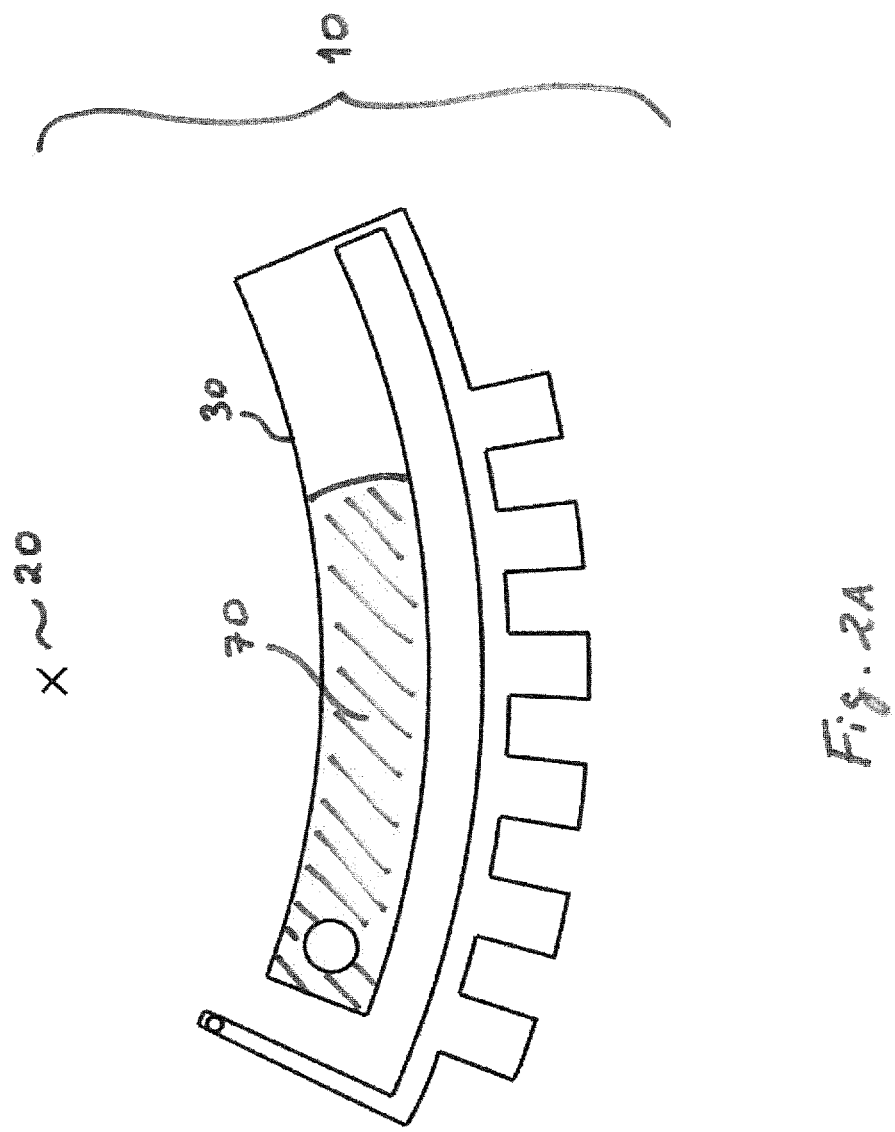

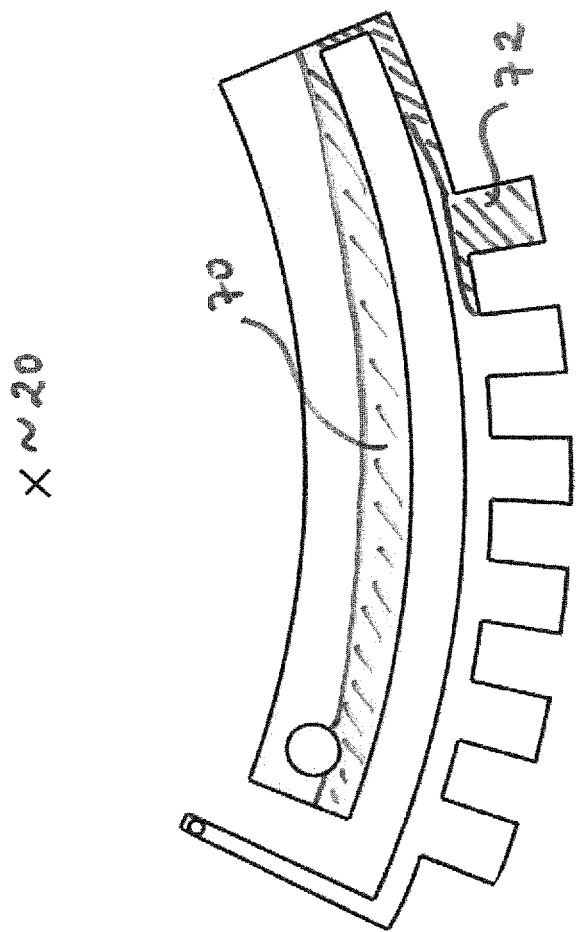

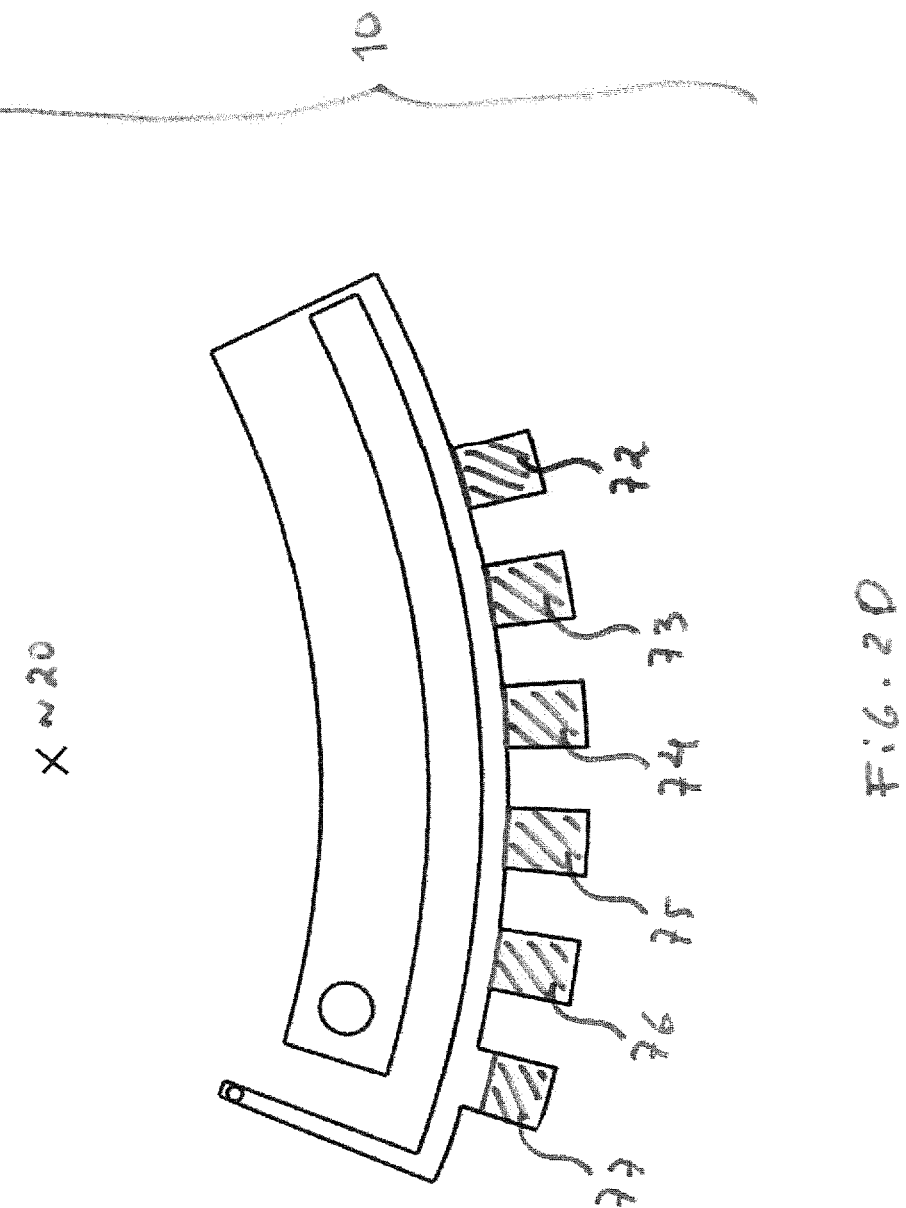

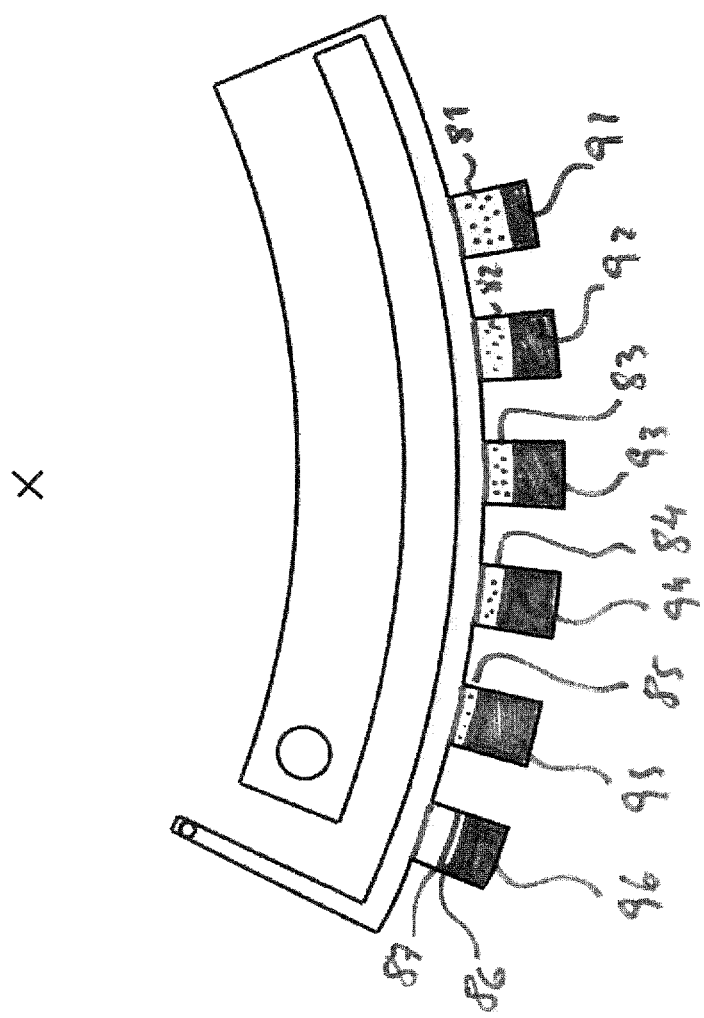

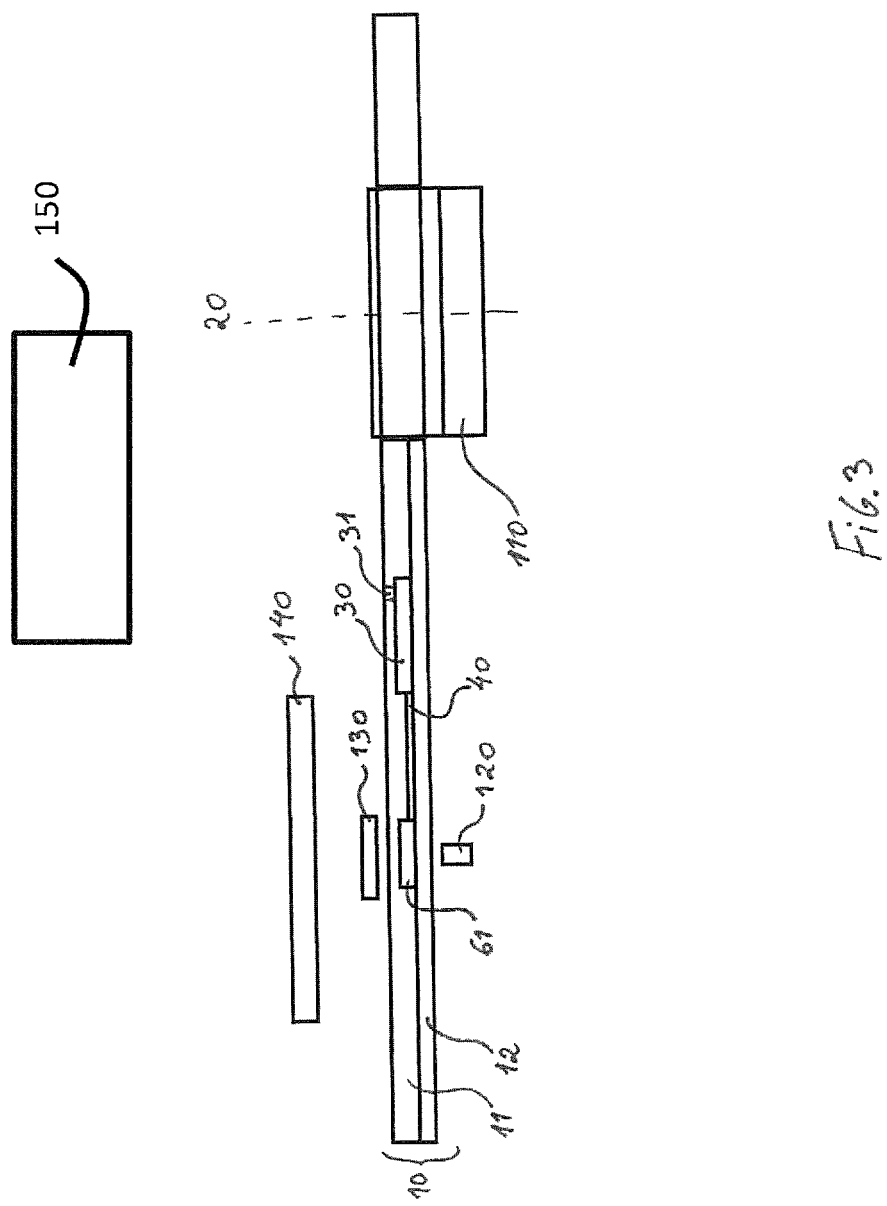

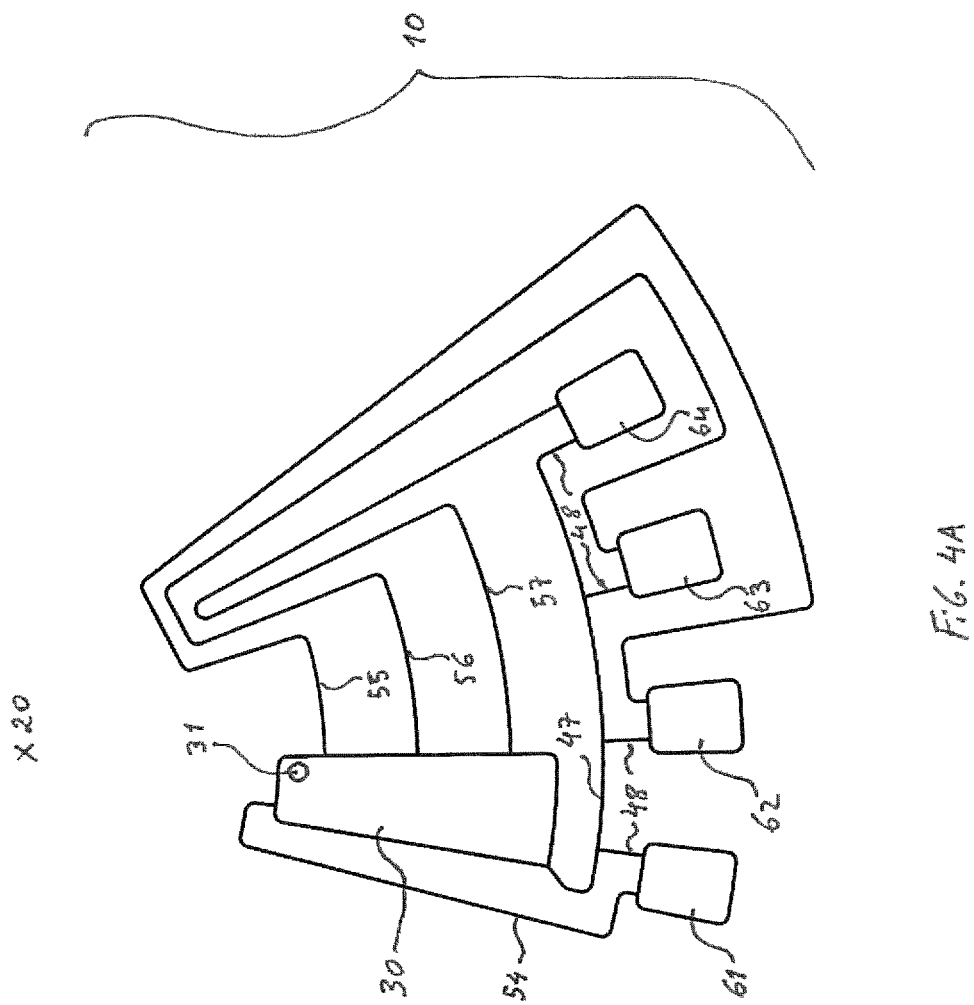

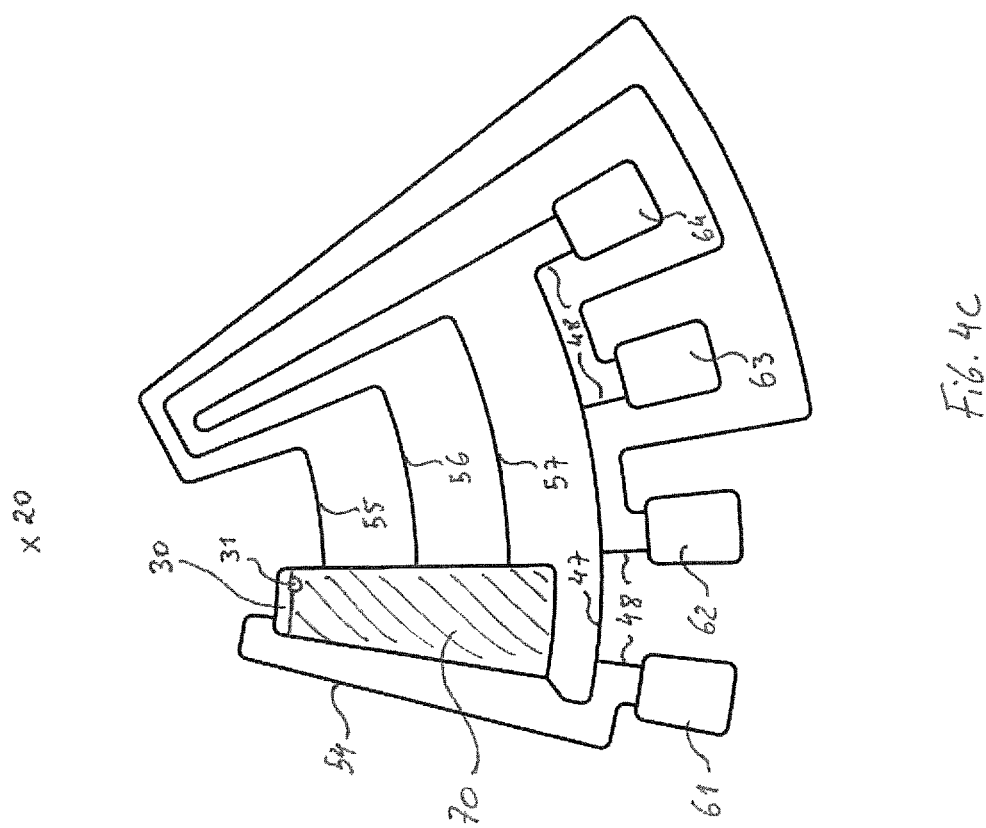

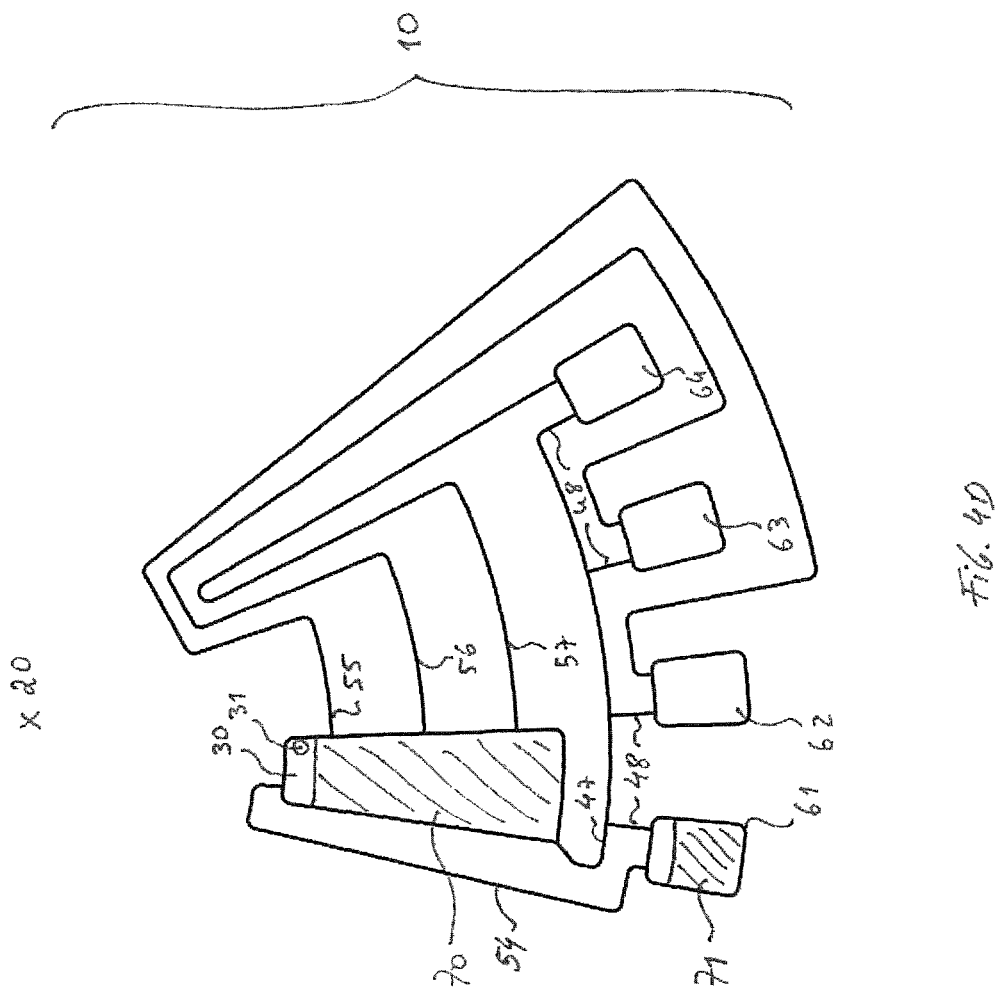

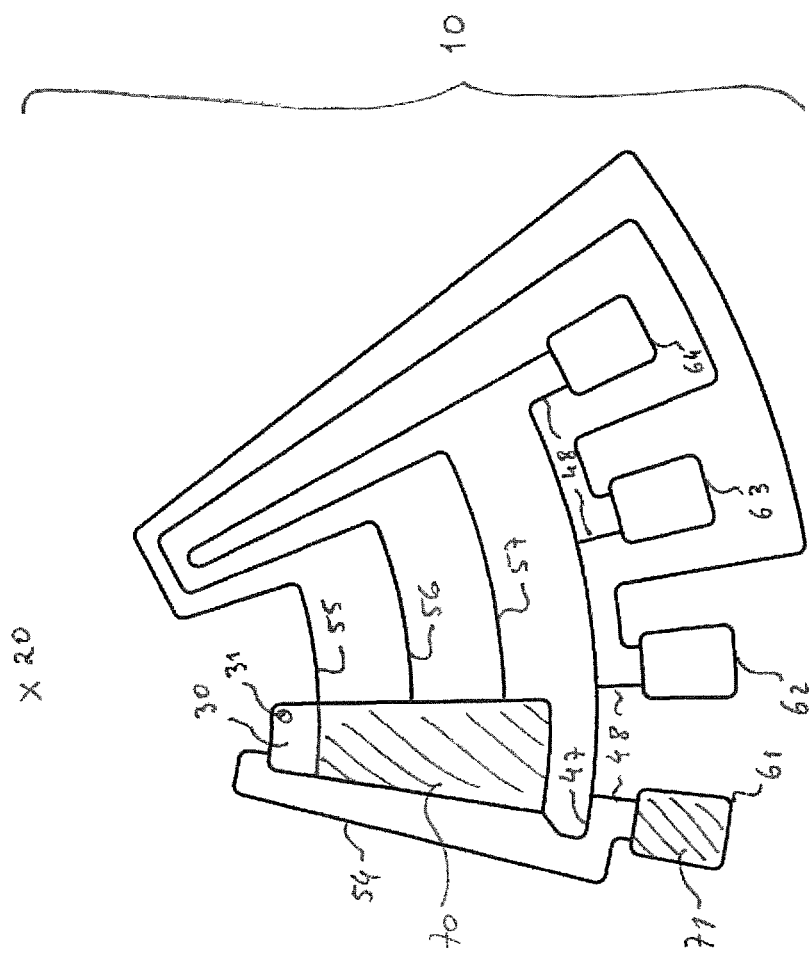

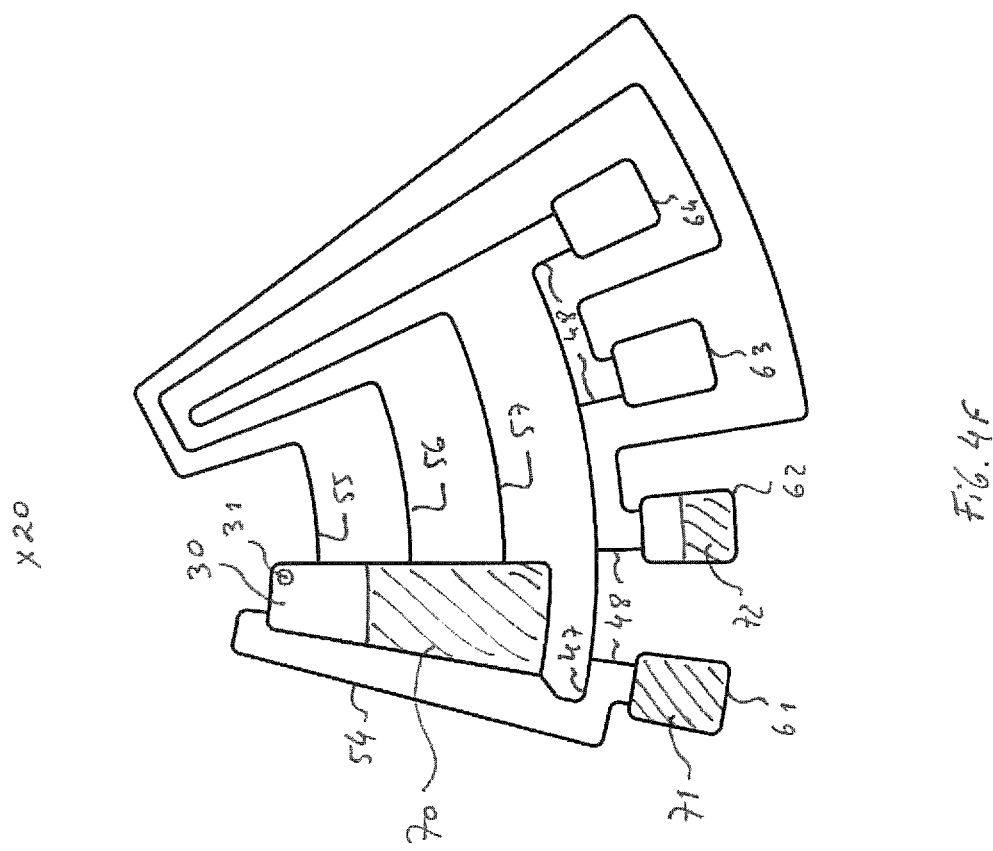

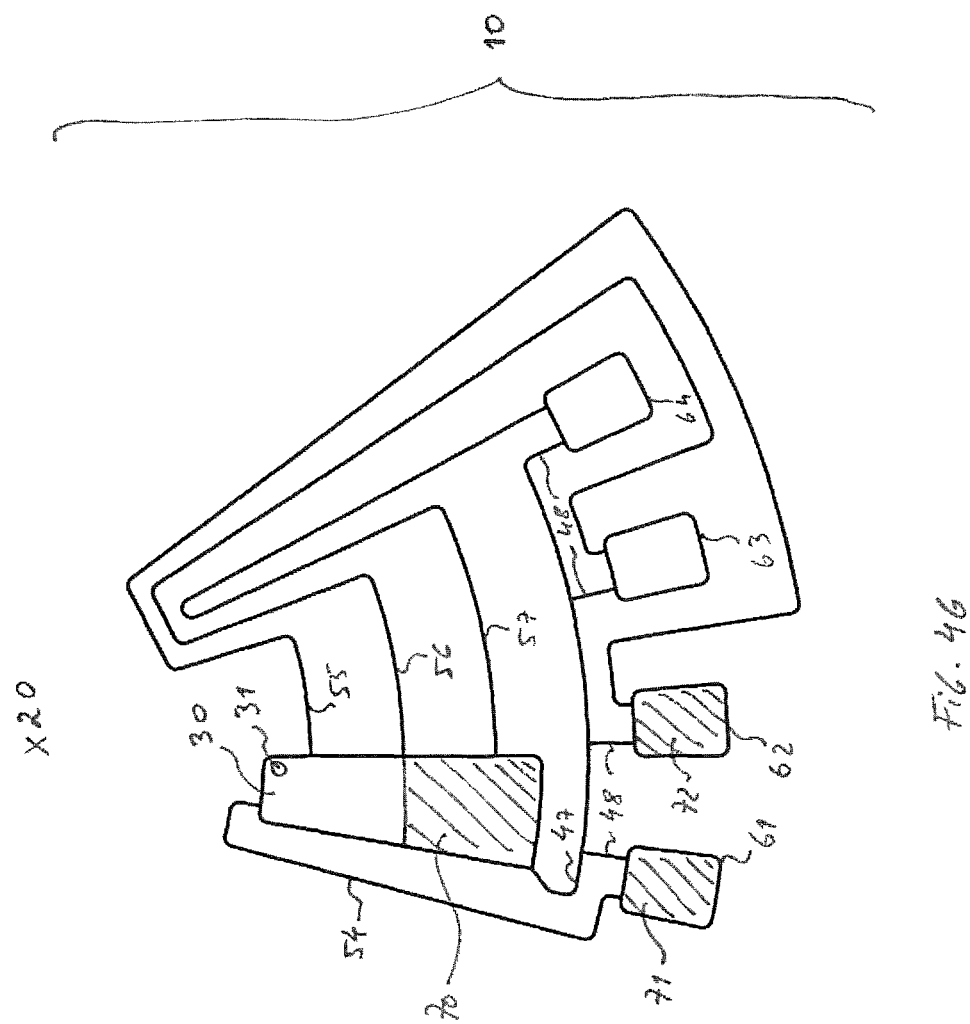

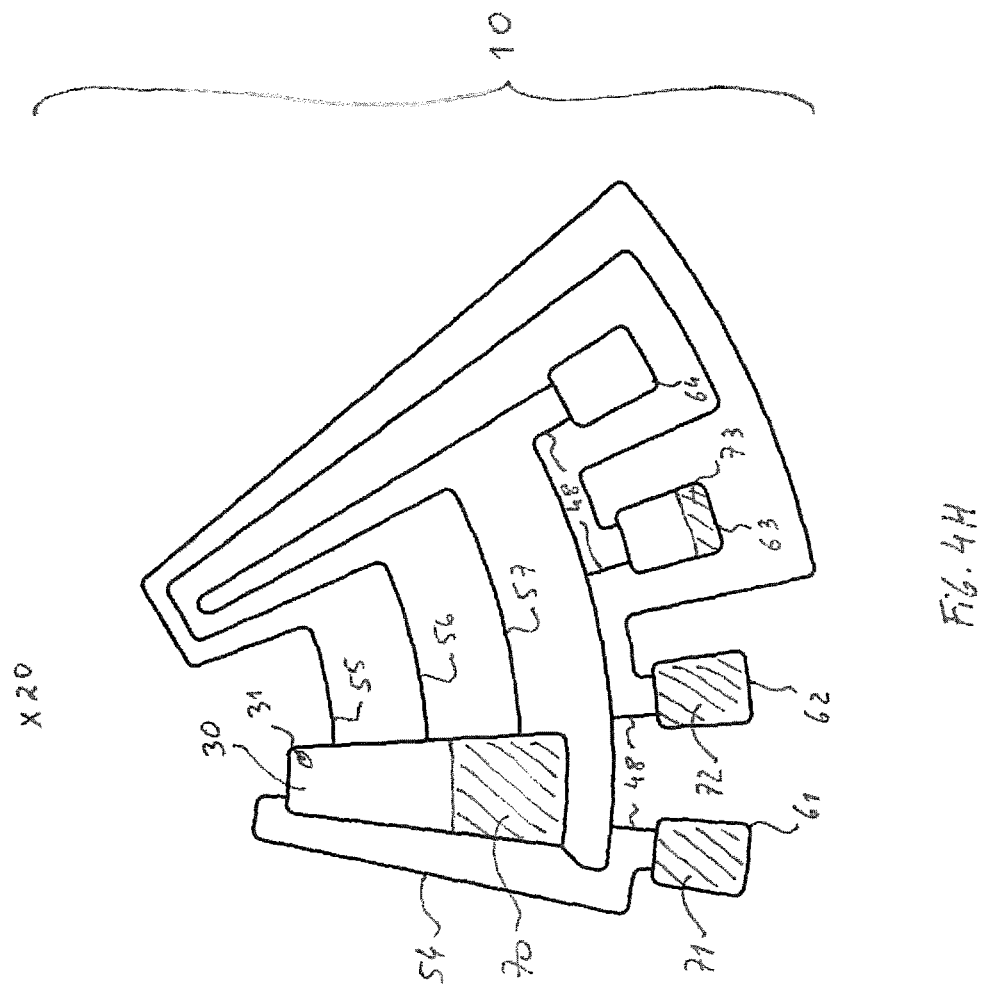

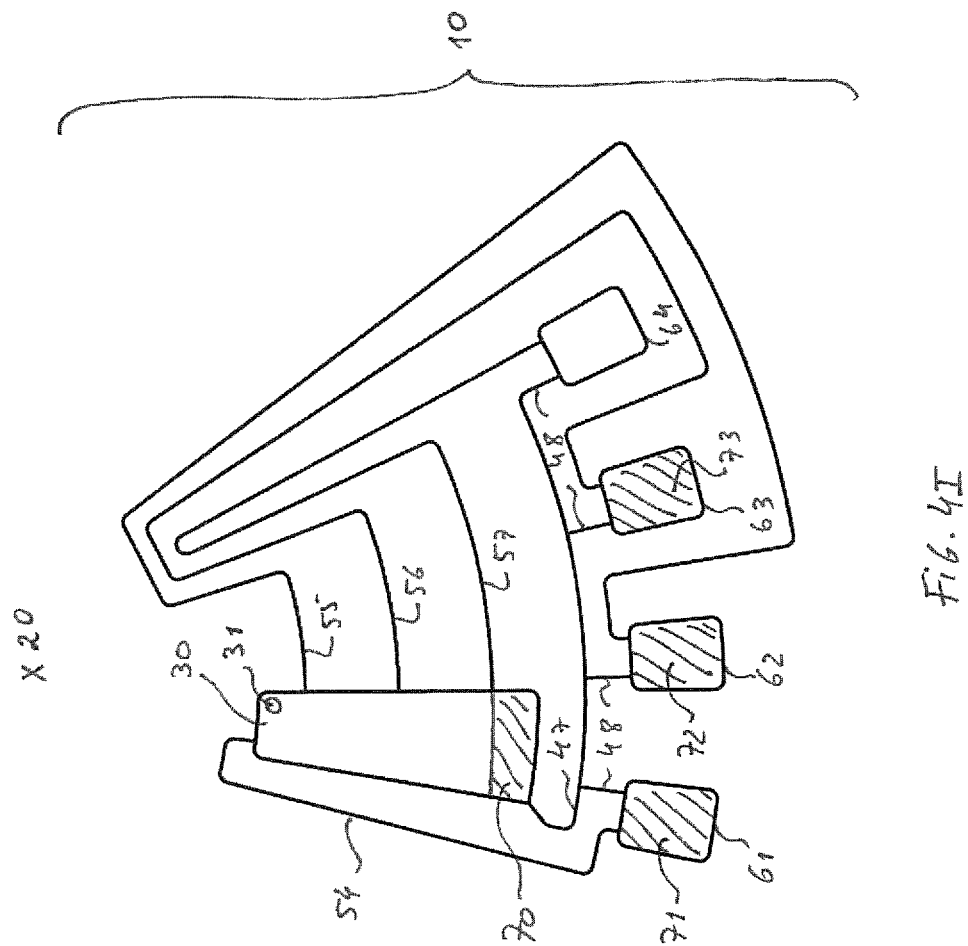

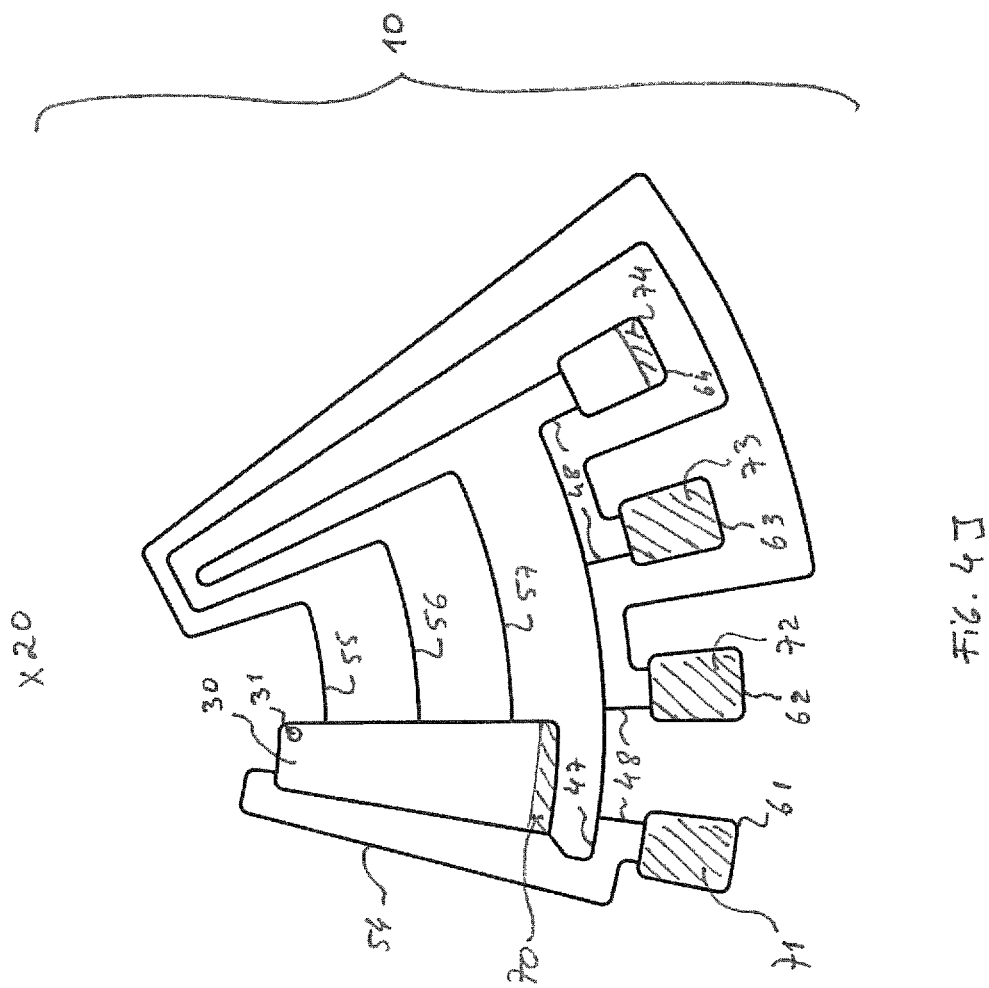

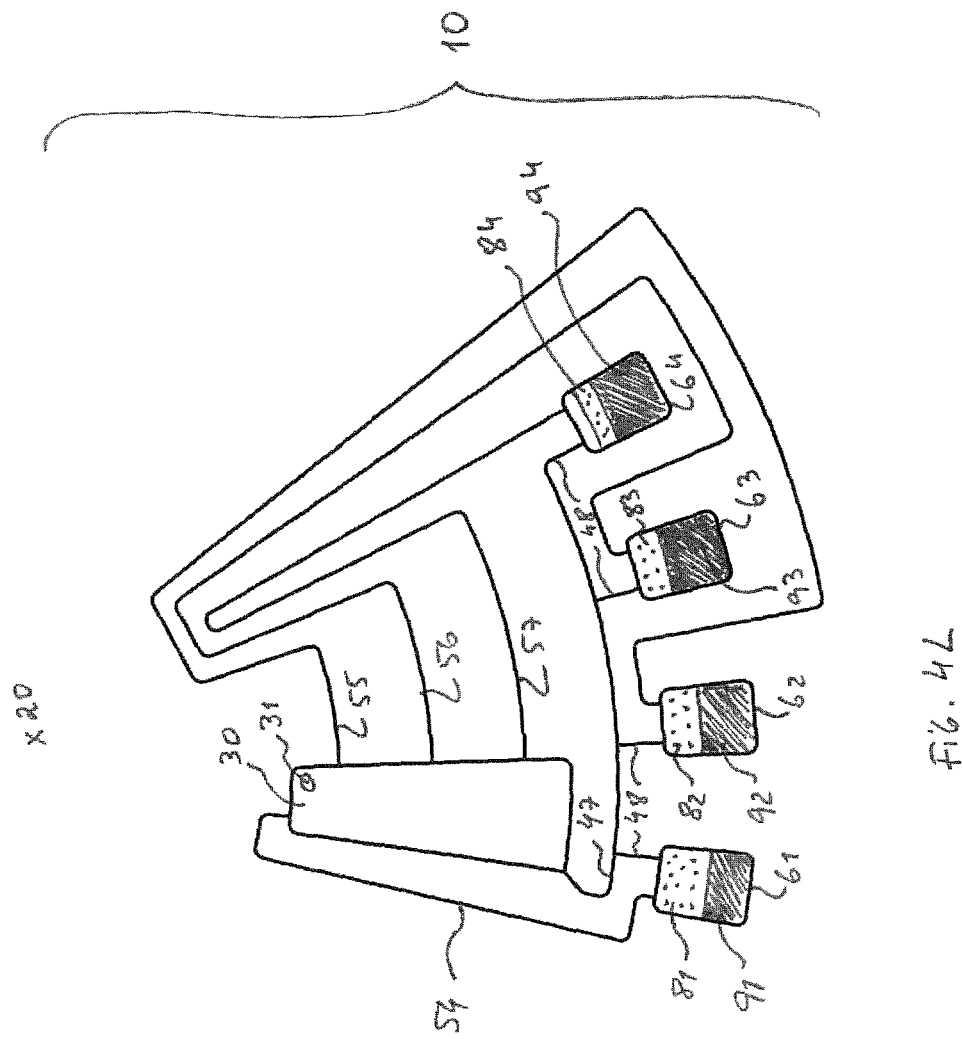

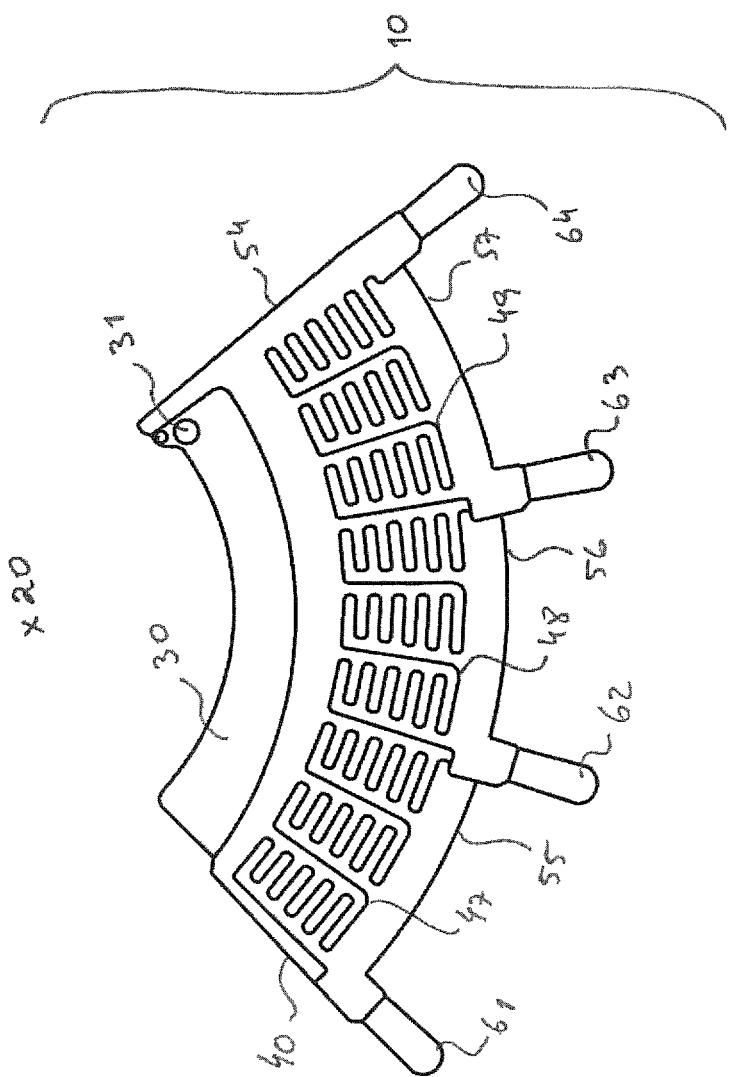

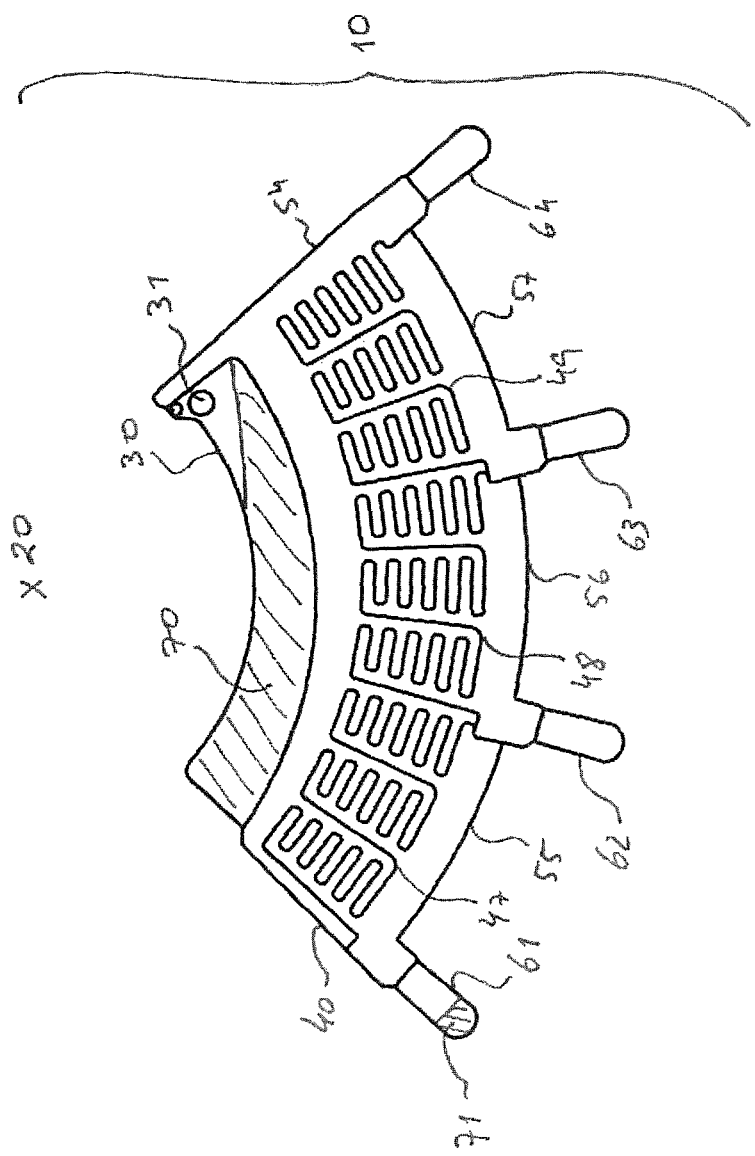

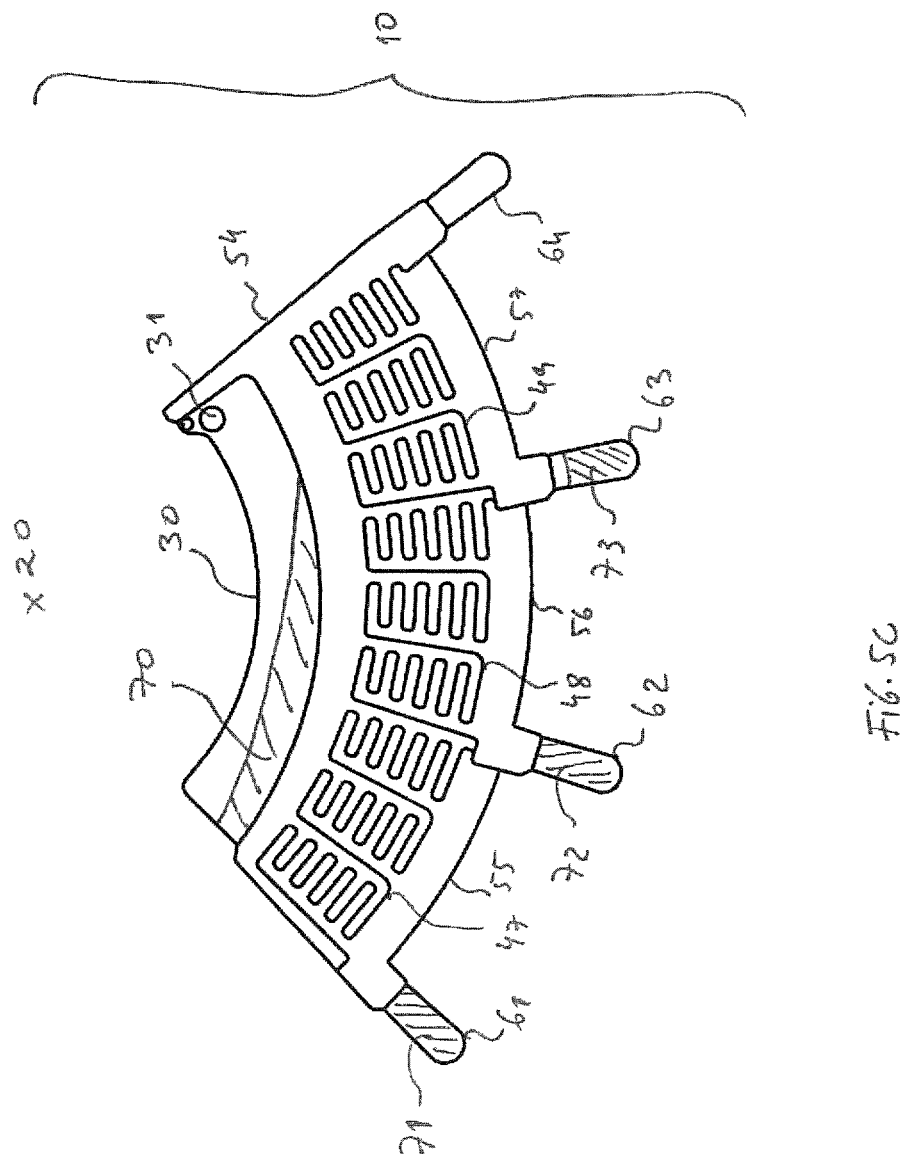

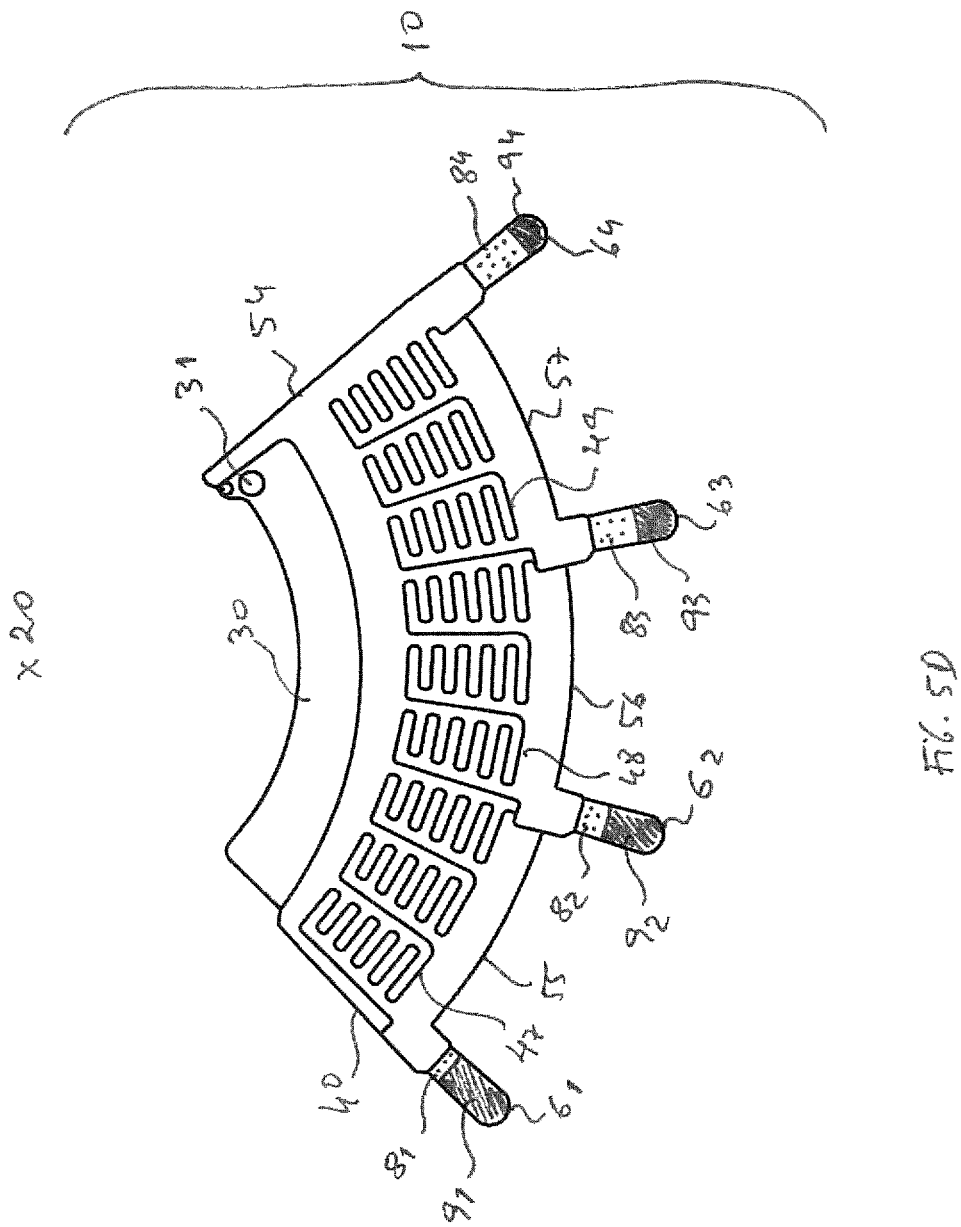

US 9,933,348 B2

SEQUENTIAL ALIQOTING AND DETERMINATION OF AN INDICATOR OF SEDIMENTATION RATE

PRIORITY CLAIM

This application is a National Phase entry of PCT Application No. PCT/EP2012/074874, filed Dec. 7, 2012, which claims priority from Portugal Application No. 106054, filed Dec. 8, 2011, and which claims priority from Portugal Application No. 106053, filed Dec. 8, 2011, the disclosures of which are hereby incorporated by referenced herein in their entirety.

FIELD OF THE INVENTION

The present invention relates to a device for sequential aliquoting of a liquid and to a method and system for analysing a liquid sample to determine an indicator of sedimentation rate of the liquid sample.

BACKGROUND OF THE INVENTION

Erythrocyte sedimentation rate (ESR) is one of the traditional tests performed on whole blood in hematology laboratories. ESR measures the distance red blood cells sediment, or fall, in a vertical tube over a given period of time. The measurement of sedimentation is calculated as millimeters of sedimentation per hour. It takes more than one hour to complete and typically requires a significant blood volume (~mL).

Hematocrit (HCT) or packed red blood cell volume is the ratio of the volume of red blood cells (expressed as percentage or as a decimal fraction) to the volume of whole blood of which the red blood cells are a component. In micromethods for determining hematocrit, tubes containing whole blood are centrifuged for 5 min at 10-12000 g to separate the whole blood into red cells and plasma. The hematocrit is calculated from the length of the blood column, including the plasma, and the red cell column alone, measured with a millimeter rule.

The conventional methods for measuring these two important blood parameters require too much time and too much blood for many applications. In particular, there is a significant need for fast ESR (or other sedimentation rate measure) and HCT diagnostic with minimal sample volume, in particular for point of care diagnostics.

Known automated methods measure the cell-plasma interface of a blood sample while rotating a cartridge holding the blood to determine both parameters by dynamic measurements. See for example Shelat et al, Am J Clin Pathol 2008; 130:127-130. These methods require complex precision hardware, in particular optical microscopy, while measuring from rotating a device. This complexity and associated costs are today a significant limitation for wide spread use of fast ESR and HCT measurements with small sample volumes.

Different devices and methods are known for processing liquids by centrifugation, exploiting phenomena at microscopic scale, leading to automated analytical systems with applications in different fields, including in the medical diagnostics domain. For automated analytical systems, there is a need for different functional modules to be included in a cartridge operated by rotation, for example aliquoting, blood plasma separation, mixing and liquid routing. These functional modules may be arranged in such ways that they operate in sequence or in parallel so as to follow a pre-defined protocol for analytical purposes.

Known aliquoting functional modules operated by centrifugation typically operate on a short time scale (in the order of seconds) and this may be a limiting fact or for some applications, where one requires controlled aliquoting for a pre-defined time. Furthermore, existing aliquoting functional modules may require a significant space in the cartridge, with additional structures for proper operation.

Therefore, there is a need for simple sequential aliquoting functional modules, operated by centrifugation, wherein the operating timescale can be controlled.

SUMMARY OF THE INVENTION

In a first aspect, there is provided a device for handling liquid. Advantageously, rotation of the device allows a sample to be sequentially aliquoted, specifically beginning to fill each of a plurality of receiving chambers at a different respective time. For the avoidance of doubt, the term "beginning to fill" is employed here to encompass both beginning to first fill from empty or beginning to fill after a previous filling event, i.e. not from empty. Specifically, the receiving chambers are filled and vented through separate (supply and vent) conduits, providing multiple design possibilities to control the sequential aliquoting.

In some embodiments, sequential aliquating is controlled via vent conduits, which are connected to suitably radially spaced vent ports. As any one vent port is covered by liquid in the reservoir chamber, the liquid head upon the vent port prevents venting of the corresponding receiving chamber, so that it is not filled. As the liquid level in the reservoir chamber drops when another chamber is filled, vent ports become progressively open/able to vent the corresponding receiving chambers. As a result, as the liquid level drops with time when filling one or more receiving chambers, vent ports become active progressively and additional receiving chambers begin to fill at corresponding different times.

It will be understood that, in this embodiment, there are many compatible ways of connecting the supply conduits, e.g. to a supply manifold or directly to the reservoir chamber. Further, by appropriate placement of a first one of the vent ports, it can be assured that no, or a low, liquid head is present for a first one of the receiving chambers to facilitate the beginning of the sequential aliquoting sequence.

In some embodiments, the timing of filling the receiving chambers can be controlled by suitably connecting the supply conduits to respective supply ports of a supply manifold. In these embodiments, venting of the receiving chambers can take in any suitable fashion, via one or more conduits to a vent conduit of the device enabling pressure equalisation with the reservoir chamber, or all chambers may be connected, directly or indirectly, to ambient gas (air) around the device.

Specifically, the vent conduit of a previous chamber in the sequence is, in some embodiments, connected to vent the previous chamber through a subsequent chamber, its supply conduit, or both. Further, to control the timing of filling, in some embodiments, the supply manifold comprises one or more meandering portions, which may extend from a first to a last one of the supply ports.

In another aspect, any one or all of the devices described above may be configured as micro-fluidic devices, i.e. having at least one fluidic element, such as a reservoir or a channel with at least one dimension below 1 mm.

In yet another aspect, there is provided a method of analysing a liquid sample. Using a sequential aliquoting step while sedimentation takes place in a liquid sample, that is starting each aliquot at a different time while sedimentation is on-going, temporal snap shots of the sedimentation process are obtained in the form of the sequential aliquots, more specifically the ratio of a lighter and a heavier phase in each aliquot. This can be "read-out" by subsequent full sedimentation of the aliquots and the detection of the position of the interface between the phases in each aliquot chamber. These positions, corresponding to temporal snapshots, contain information on sedimentation rate and can be used to derive an indicator of sedimentation rate in various forms (e.g. a rate, a high/low/normal classification).

In particular, in some embodiments, the liquid is blood and the phases are serum and cellular material. The method may further comprise deriving a total volume or fraction of the denser phase (hematocrit in the case of blood). Further, in some embodiments, the total aliquoted volume can be derived from detected interface positions, as a quality control measure. This may be based on detecting all individual aliquoting volumes, or only the last one on the assumption that the previous ones were filled fully or to an otherwise known extent.

In some embodiments, the methods uses a rotating device to drive sedimentation and sequential aliqoting by rotating a device comprising both sedimentation and aliquoting chambers. In some specific embodiments, the device is configured as the devices for containing liquid described above.

In another aspect, there is provided a system comprising a detector and a processor coupled to the detector, configured to implement a method as described above. In some embodiments, the system comprises a motor for rotating a liquid containing device to drive liquid flow as described above.

In overview, some embodiments of a method of determining an indicator of sedimentation rate includes obtaining performing in a rotatable cartridge, sequential aliquots of an initial known blood volume while performing centrifugation of the said blood, in a controlled manner, obtaining multiple aliquots while blood cells are being sedimented but not fully sedimented while the aliquoting process is taking place. One obtains in this way different volumes of blood having different fractions of cells and plasma. The different partially sedimented blood aliquots are then fully sedimented by applying further centrifugation, and then the cartridge is stopped or its rotational speed sufficiently reduced and static optical measurements are performed to determine the cell fraction of each blood aliquot by measuring each cell-plasma interface. Finally, an indicator of sedimentation rate is derived, for example comparing the measurements with pre-defined calibration values to determine both Erythrocyte sedimentation rate and Hematocrit.

Some embodiments of liquid handling devices explore gas pressure imbalances in a cartridge operated by centrifugation, in order to achieve sequential liquid delivery from a single upstream chamber into multiple downstream chambers. The basic principle of some of these embodiments relates to pressure balance channels connecting each downstream chamber with the upstream chamber, placed in such positions that they are normally closed while liquid is above a certain level in the upstream chamber, and become open when the liquid is below a certain level in the upstream chamber. By arranging the positions of the different pressure balance channels and by operating the device in sufficiently low rotational speeds, one may obtain sequential flow from the upstream chamber into the multiple downstream aliquots on a controllable timescale.

BRIEF DESCRIPTION OF THE FIGURES

Embodiments are now described by way of example only to illustrate aspects and principles of the present disclosure, with reference to the accompanying drawings in which:

FIGS. 2A to 2E illustrate operation of the cartridge of FIG. 1;

FIG. 3 illustrates a system for measuring an indicator of sedimentation rate and hematocrit of blood;

FIG. 4A illustrates an alternative blood aliquoting device;

FIGS. 4C to 4L illustrate the operation of a device in accordance with FIGS. 4A or 4B;

FIG. 5A illustrates yet another alternative blood aliquoting device; and

FIGS. 5B to 5D illustrate operation of the device of FIG. 5A.

DETAILED DESCRIPTION OF THE FIGURES

In overview, in some embodiments, a rotatable cartridge is used to obtain multiple sequential aliquots of a blood sample while performing centrifugation of the blood, in a controlled manner. The sequential aliquoting is performed is such a manner that blood cells are being sedimented but not fully sedimented while the aliquoting process in taking place.

Figure 1:
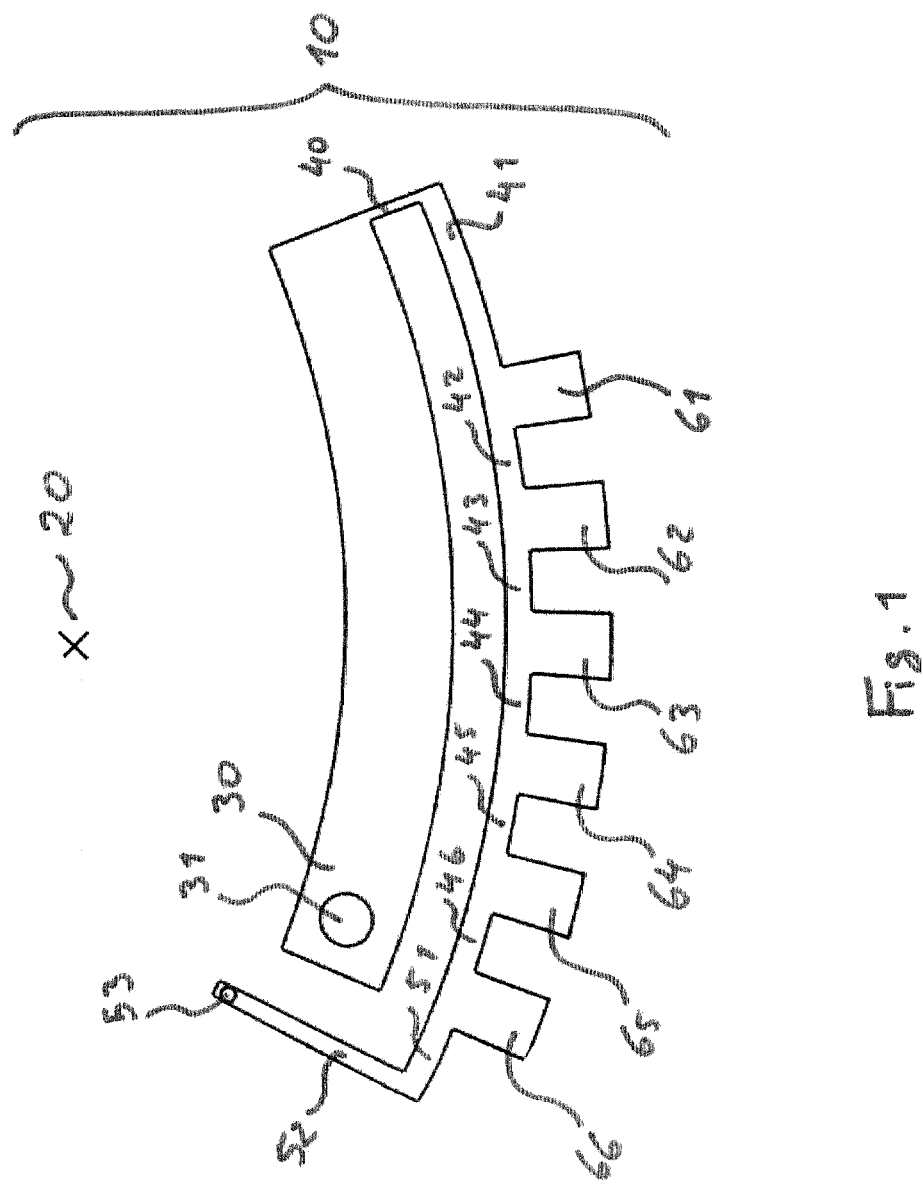
FIG. 1 illustrates a portion of a cartridge for dividing a blood volume into sequential aliquots while the blood is being partially sedimented.

FIG. 1 illustrates a portion of a cartridge (10) configured for sequential aliquoting, wherein a first blood volume is divided into sequential aliquots while the blood is being partially sedimented. The cartridge (10) is rotatable about an axis (20), and has a sample chamber (30) and a blood inlet (31) to the sample chamber (30). The sample chamber (30) is connected to multiple aliquot chambers by channels (40) and (41). A first aliquot chamber (61) is connected to a subsequent aliquot chamber (62) by a channel (42). Multiple aliquot chambers (61), (62), (63), (64), (65) and (66) are connected together by channels (42), (43), (44), (45), (46). A last aliquot chamber (66) is configured in such a way as to receive a last sample aliquot. Channels (51) and (52) are used for air ventilation when liquid flows, and an air hole (53) enables air to escape while the device is operated.

Operation of the cartridge (10) is now described with reference to FIGS. 2A to 2E.

FIG. 2A illustrates an initial position of blood (70) in the sample chamber (30) while the cartridge (10) is stopped. The blood (70) is contained radially inward in the sample chamber (30).

Figure 2B:
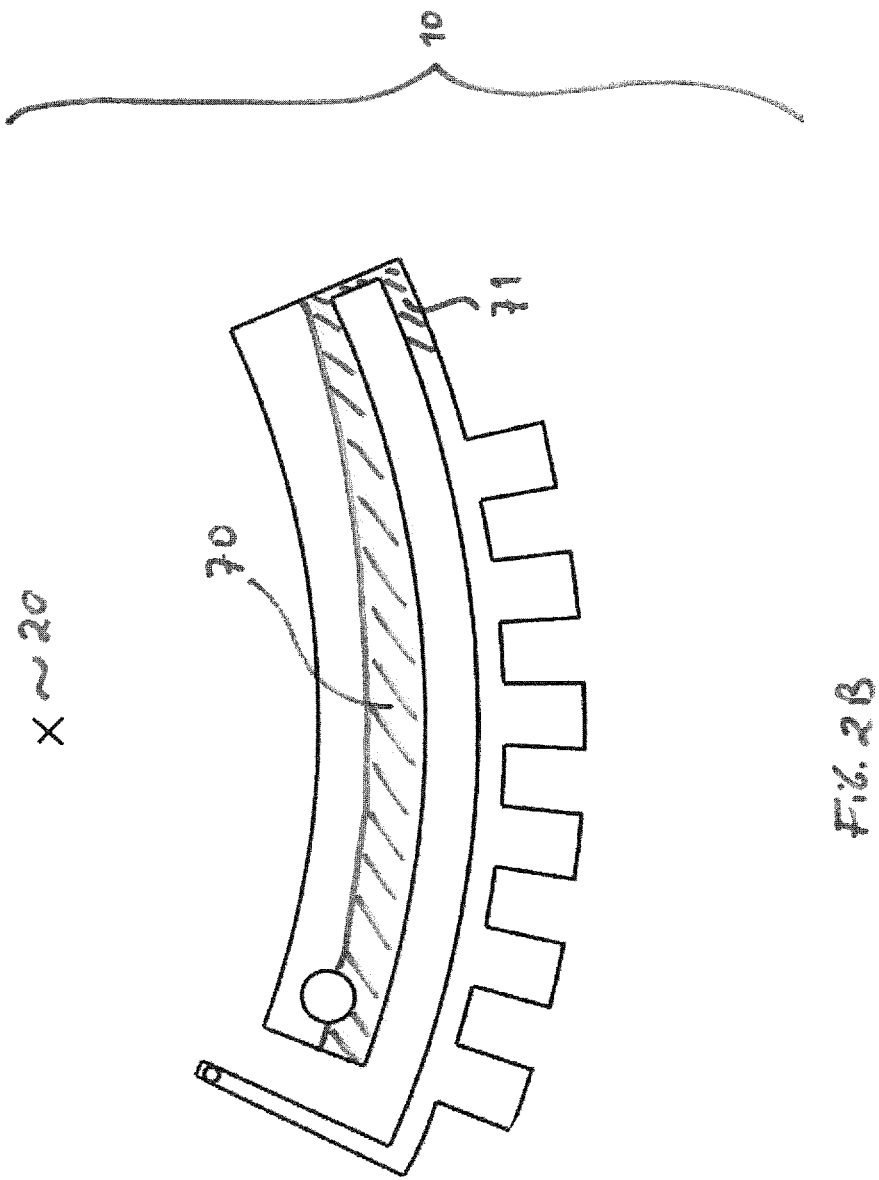

FIG. 2B illustrates an initial operational states of the cartridge (10), when the blood is forced by centrifugation to start flowing from the blood chamber (30) into the channels (40) and (41). The device is built and operated in such a way that the blood flowing in the channel (41) already is subject to cell sedimentation. This is achieved by making the channels (40) and/or (41) sufficiently small to slow liquid flow to allow partial sedimentation to occurs before the first aliquot chamber (61) is filled.

FIG. 2C illustrates a subsequent operational state of the cartridge (10), when partially sedimented blood (72) already has filled the initial aliquot chamber (61) and further advances in the channel (42) while the blood is being partially sedimented.

FIG. 2D illustrates a further subsequent operational state of the cartridge (10), when the last aliquot chamber (66) is filled, and blood is still not fully sedimented. The volume of the last blood aliquot (66) is such to contain a last portion of blood sample, while not being completely filled.

The respective filling times of each aliquot chamber are defined mostly by the shape of the chambers and channels, radial positions of the sample chamber (30) and of each aliquot chamber, the liquid head in the sample chamber (30) and the rotational speed. These filling times are thought to be roughly independent of the blood sedimentation rate of the blood sample.

FIG. 2E illustrates a final operational state of the cartridge (10), when blood in all aliquot chambers (61-66) are fully sedimented by centrifugation. In the first aliquot chamber (61), the relative volume fractions of blood cells (91) and blood plasma (81) are significantly different from the relative volume fractions of blood cells and blood plasma of the other aliquots, since the aliquots were obtained at different times during the sedimentation process. The last aliquot chamber (66) contains not only the interface between the blood cells (96) and the blood plasma (86) but also an interface (87) between blood plasma and air, since the chamber (66) is not fully filled.

At this time, the cartridge (10) is stopped or its rotational speed sufficiently reduced to measure the position of interfaces between blood cells and blood plasma, as well as the plasma/air in the last aliquot chamber interface (87) by optical means. Knowing the shape, depth and dimensions of each aliquot chamber enables the determination of both an indicator of sedimentation rate and haematocrit, as described below.

FIG. 3 illustrates a system used for measuring an indicator of the sedimentation rate and hematocrit of a blood sample according to the present invention. The cartridge is placed in a rotor (110) driven by a BDLC motor controlled for precise rotational speed up to 100 Hz, rotatable along the axis (20) and light from a light source (120) is incident to a specific region of the cartridge where measurements are to be made. An optical imaging sensor (140) with focusing lenses (130) is used for the determination of each interface position described above. The cartridge (10) is composed of two bonded parts (11) and (12) with the fluidic structures (30), (31), (40), (61), etc being defined in the upper part (11). A processor (150) is connected to the optical image sensor (140) and has access to calibration information. The image sensor (140) determines the positions of each interface of blood cells and blood plasma of each blood aliquot chamber, and from this information the processor estimates an indicator of the blood sedimentation rate and further the Hematocrit of blood.

The estimation of the indicator and hematocrit is now described. Because the blood in each aliquot chamber (61-66) was extracted at a different time during sedimentation, it contains different volume ratios of plasma and cellular material. The difference in volume ratios from one aliquot to the next therefore is related to the rate of sedimentation, as the aliquots, in effect, are snapshots of the sedimentation process.

The information contained in the different plasma/cellular material volume ratios can be extracted by a final step of full sedimentation of the aliquots, separating plasma from cellular material to form an interface therebetween. Subsequent to full sedimentation, the position of the interface relative to each respective aliquot chamber, which is directly indicative of the volume ratios (and from which the latter can be derived, if desired) is measured.

The processes underlying blood sedimentation are complex, but it is well-known that the sedimentation process roughly follows a sigmoid progression with a roughly linear middle region followed by a saturation region. To some extent depending on the construction and operation of the cartridge (10) (and hence the region on the sedimentation curve in which the sample was sequentially aliquoted) a number of techniques can be employed to derive an indicator of sedimentation rate.

In a first embodiment, the cartridge (10) and its operation are configured such that the aliquots are extracted in a linear range, or a linear range is detected by analysing the ensemble of detected interface position with the processor (150). The processor then applies linear regression to determine the slope of interface positions versus the corresponding position of the aliquot in the sequence of aliquots as the indicator. In a variant of this embodiment, the processor takes pairwise differences of the measured positions of adjacent aliquots in the linear range and averages these differences.

In a second embodiment, in particular suitable if a larger number of aliquots is obtained, say 5, 10 or more, the cartridge and its operation are configured such that sedimentation saturates/is fully or near fully complete during sequential aliquoting. The processor (150) then determines the identity of the first aliquot for which there is no change (or a change smaller than a threshold amount) from the previous aliquot as the indicator of sedimentation rate.

In a third embodiment, the processor (150) selects between the first and second embodiment after a preliminary step of analysing the detected positions to select between the first embodiment (at least some aliquots are in the linear range), the second embodiment (saturation occurs), or both.

In a fourth embodiment, the portions of the interfaces themselves are taken as a multivariate indicator of sedimentation rates.

In any of the above embodiments, the indicator may be used (e.g. stored or displayed by a display) or may be further processed using calibration data. For example, the indicator may be transformed or calibrated to provide a binary or otherwise classification (e.g. high or low; normal or abnormal; high, normal or low) or to report in a different scale, for example mm/h according to the widely used Westergren method.

Hematocrit is measured, in some embodiments by adding the volumes of cellular material in each aliquot based on the detected interface positions and aliquot chamber geometry, divided by the known sample volume. Alternatively, the sample volume can be calculated, as well, based on the geometry of all aliquot chambers and the air/plasma interface in the last aliquot chamber. Since sedimentation rate is known to be influenced by hematocrit, the derived value of haematocrit is used in the determination of the sedimentation rate indicator in some embodiments, specifically used to select a sigmoid fitting function in variants of the first embodiment where non-linear fits are used to derive the indicator as a set of parameters of the non-linear fitting function. In some other embodiments, hematocrit is used to aid calibration against the Westergren method.

A specific implementation of a device is now described. The cartridge (10) consists of two disk-shaped parts of 0.6 mm thickness each bonded together, having an outer diameter of 120 mm and an inner hole of 15 mm diameter centered at the rotational axis (20). The chamber (30) is of 0.2 mm depth engraved into the upper cartridge part (11) having an average radius of 20 mm from the rotational axis (20) and being capable of holding 12 µl of blood. The channels (40), (43), etc have a thickness of 0.05 mm and 1 mm width. The aliquot chambers (61-66) have a depth of 0.2 mm and a volume of 2 µl each. Their entrance width is of 2 mm. The motor (110) is a step motor controlled both for precise positioning (better than 0.04° per micro-step) and high rotational speed (up to 100 Hz). The image sensor (140) consist of a CCD camera with integrated autofocus, and the light emitter (120) consist of a white LED.

A specific implementation of a method using the above implementation to measure the Erytrocyte Sedimentation Rate or a related indicator and Hematocrit is now described.

First, 12 µl of blood are inserted into the blood inlet (31) of the sample chamber (30). Then the blood inlet (31) is sealed, in order to prevent blood escaping from the cartridge (10). Then the cartridge (10) is placed in the rotor (110) and rotated at 20 Hz. After 15 seconds the first blood aliquot (61) is filled, after 31 s the second blood aliquot (62) is filled, after 49 seconds the third blood aliquot (63) is filled, after 70 seconds the forth blood aliquot (64) is filled, after 95 seconds the fifth blood aliquot (65) is filled and after 125 seconds the final blood aliquot (66) is partially filled and flow stops since all blood is moved from the initial blood chamber (30). Then the motor (110) rotates at 50 Hz for 55 s and then gently stops. Then the cartridge (10) is precisely rotated so the optical system scans each blood aliquot (61), (62), (63), (64), (65) and (66) and positions of each interface are recorded. Then, the positions of each interface are compared with calibration data and results of an indicator of sedimentation rate and hematocrit are finally determined.

One other implementation is now detailed:

First, 15 µl of blood are inserted into the blood inlet of the sample chamber. Then the blood inlet is sealed, in order to prevent blood escaping from the cartridge (10). Then the cartridge (10) is placed in the rotor (110) and rotated at 20 Hz. After 15 seconds the first aliquot chamber (61) is filled, after 31 s the second aliquot chamber (62) is filled, after 49 seconds the third aliquot chamber (63) is filled, after 70 seconds the forth aliquot chamber (64) is filled, after 95 seconds the fifth aliquot chamber (65) is filled and after 125 seconds the final aliquot chamber (66) is partially filled and flow stops since all blood is moved from the initial blood chamber (30). The cartridge is then rotated at 50 Hz for 55 s and then gently stopped. Then the cartridge is precisely rotated so the optical system scans each blood aliquot and positions of each interface are recorded. Then, the positions of each interface are compared with calibration data and results of sedimentation rate and hematocrit are finally determined.

The channels (40) and (41) may have preferably depths below 0.5 mm, more preferably below 0.2 mm and more preferably below 0.1 mm. The same conditions may apply to the other channels. Channel may have preferable widths below 0.5 mm, more preferable below 0.25 mm. In one embodiment of the present invention, the cannel (40) may contain a more significant constriction to minimize liquid flow, is some cases preferably below 0.1 mm depth and 0.1 mm width, or even below 0.025 mm depth and 0.1 mm width. For precise measurements the blood flow should be sufficiently slow when compared to the blood sedimentation time scale, but not too slow, since each blood aliquot must be only partially sedimented while filled. One obtains in this way different volumes of blood having different fractions of cells and plasma. The different blood aliquots partially sedimented are then fully sedimented by applying further centrifugation, and then the cartridge is stopped and static optical measurements are performed to determine the cell fraction of each blood aliquot by measuring each cell-plasma interface. Finally, the measurements are compared with pre-defined calibration values and both Erythrocyte sedimentation rate and Hematocrit determined.

The cartridge illustrated in FIG. 2A to FIG. 2E requires a small working window of rotational speeds, to achieve appropriate flow rates for sequential aliquoting. If the rotation rate is too high, the blood cells could sediment too fast while blood is flowing in the channel on top of each aliquot structure and replace the less dense blood plasma. This may lead to a distribution of cells and plasma not clearly related to the blood sedimentation rate. The dimensions of each aliquot chamber may be optimized in order to minimize this effect. Other aliquoting structures will now be discussed that can be used for sedimentation rate measurements and may be considered preferable in some applications since they may be operated in a more broader rotational speed range to achieve sequential aliquoting during sedimentation.

FIG. 4A illustrates an alternative cartridge (10) suitable for sequential aliquoting and sedimentation rate measurements and for use with a system as described with reference to FIG. 3. A blood sample is inserted into the blood inlet (31) of the sample chamber (30), the latter being connected to multiple aliquot chambers (61), (62), (63) and (64) by a distribution channel (47) and connecting channels (48). Each chamber (61), (62), (63) and (64) is connected to the sample chamber (30) by pressure balance channels (54), (55), (56) and (57), connected to the sample chamber (30) at radially spaced vent ports.

When the sample chamber (30) is filled, the pressure balance channels (55), (56) and (57) are closed and the pressure imbalance that would result from flow into the receiving chambers may prevent normal flow to the aliquot chamber (62), (63) and (64). The first aliquot chamber (61) has its pressure balance channel (54) connected to a radially innermost aspect of the sample chamber (30), such that the corresponding vent port is free of liquid (or, if not open, experiences the lowest pressure head of the pressure balance channels at their respective vent ports). Therefore, as a result of centrifugal force, the first aliquot chamber (61) fills with liquid, while the liquid head on the vent ports associated with the other aliquot chambers prevents pressure equalisation and hence flow to these other aliquot chambers.

Figure 4B:
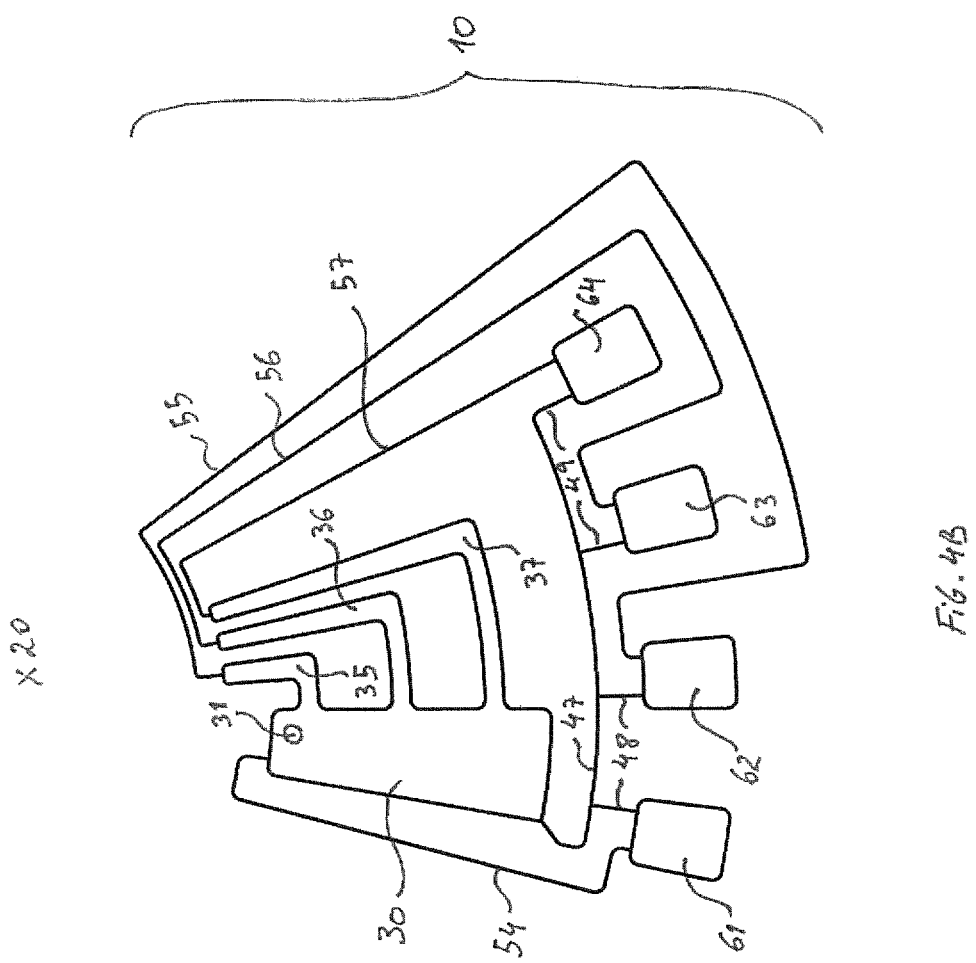
FIG. 4B illustrates a variant of the alternative blood aliquoting device.

In some cases, when surface tension properties of liquids and materials used are two similar, the pressure balance channels (55), (56) and (57) may fill with liquid by capillary action and prevent proper work of the device. In order to minimize this effect, a slightly different configuration of the sample chamber (30), illustrated in FIG. 4B, is used in some embodiments. The cartridge (10) is configured as described above but with the connection of the pressure balance channels (55), (56) and (57) into the sample chamber (30) being configured as an protrusion from the sample chamber (30) with sufficiently large sections (35), (36) and (37) to prevent normal flow of liquid by capillary action from the chamber (30) into the pressure balance channels (55), (56) and (57).

A method of operation of the cartridge (10) for sequential aliquoting does not depend on the implementation the device according to either FIG. 4A or FIG. 4B and is now described with reference to FIG. 4C to FIG. 4L.

FIG. 4C illustrates the initial placement of a blood sample (70) in the sample chamber (30) while the cartridge (10) is stopped. The blood sample (70) is contained in the more radial inward part of the sample chamber (30) and there is no flow while the cartridge is not rotating.

FIG. 4D illustrates a second operational state of the cartridge (10), when the cartridge is being rotated about the rotation axis (20). The blood flows due to centrifugation into the aliquot chamber (61), since channel (54) enables the pressure balance to be maintained while liquid flows. There is no flow into the other aliquot chambers (62), (63) nor into the aliquot chamber (64), since their respective pressure balance channels (55), (56) and (57) are closed by a liquid head and therefore any liquid flow would represent a significant air pressure increase. The rotation rate is chosen such that the portion of blood (71) placed into the aliquot chamber (61) is not fully sedimented. The cartridge (10) remains in this state until the liquid level in the sample chamber (30) is below the level of the vent port connected to the pressure balance channel (55).

FIG. 4E illustrates a third operational state of the rotatable cartridge (10), when the cartridge (10) is being rotated about the rotation axis (20), when the liquid level in the sample chamber (30) drops below the vent port of the pressure balance channel (55).

As the liquid in the sample chamber drops as the chamber (62) fills when its pressure balance channel (55) is open (and the aliquot chamber (61) fills to its maximum level), the liquid level in the sample chamber (30) drops further, until the vent port of the pressure balance channel (56) is uncovered and liquid flows into aliquot chamber (63), and so on until all sample liquid has been dispensed sequentially to the aliquot chambers (61-64).

The radial spacing of the vent ports may be designed so that the first aliquot chamber (61) does not fill completely (more precisely, any liquid level in the pressure balance channel (54) does not rise to the liquid level in the sample chamber (30), before the next vent port (connected to pressure balance channel 55) is opened. Otherwise, emptying of the sample chamber (30) could come to a halt and liquid flow stop with the liquid level of the sample chamber (30) still above the level of the vent port connected to the pressure balance channel (55). Placing the vent ports such that the chamber (or downstream volume) connected to a vent port is larger than the volume between that vent port and the next one ensures that vent ports are uncovered before filling of their respective chambers begins. If this is not the case some of the centrifugal force would be needed to overcome any remaining liquid head, possibly leading to lower flow rates or, in some cases, cessation flow.

FIG. 4F illustrates a fourth operational state of the cartridge (10), when the cartridge is being rotated about the rotation axis (20) and the sample liquid flows by centrifugation and with pressure equilibrium into the aliquot chamber (62).

FIG. 4G illustrates a fifth operational state of the cartridge (10), when the cartridge is being rotated about the rotation axis (20) and the vent port of the channel (56) becomes uncovered.

FIG. 4H illustrates a sixth operational state of the cartridge (10), when the cartridge is being rotated about rotation axis (20) and the sample liquid flows by centrifugation and with pressure equilibrium into the aliquot chamber (63).

FIG. 4I illustrates a seventh operational state of the rotatable cartridge (10), when the cartridge is being rotated about the rotation axis (20) and the vent port of the channel (57) becomes uncovered.

FIG. 4J illustrates an eighth operational state of the rotatable cartridge (10), when the cartridge is being rotated about the rotation axis (20) and the sample liquid flows by centrifugation and with pressure equilibrium into the aliquot chamber (64).

Figure 4K:
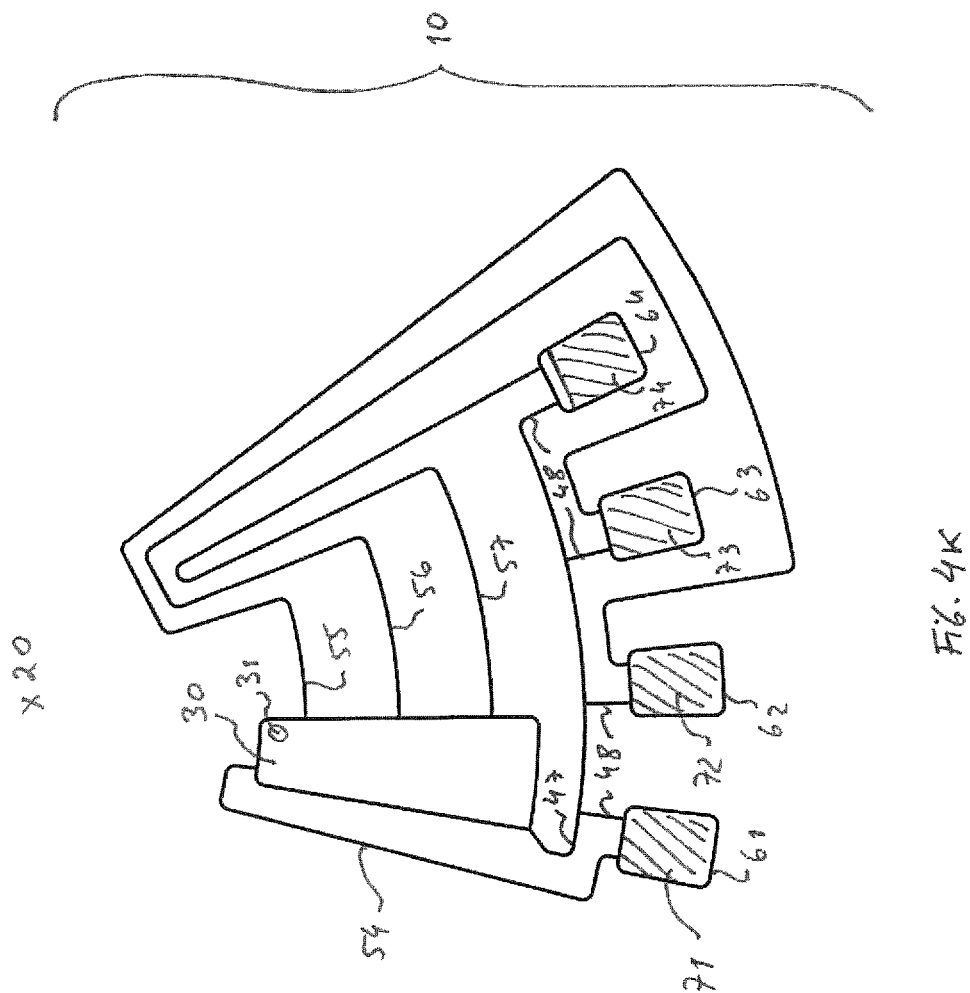

FIG. 4K illustrates a ninth operational state of the rotatable cartridge (10), when the cartridge is being rotated along the rotation axis (20) and the chamber (30) has been fully emptied of blood.

At this stage, the cartridge (10) contains different blood aliquots each with a different cell volume percentage since the aliquoting process occurred while blood was being partially sedimented.

FIG. 4L illustrates a tenth operational state of the rotatable cartridge (10), when the cartridge is further rotated about the rotation axis (20), and each blood aliquot in the aliquot chambers is fully sedimented, having each aliquot a different cell percentage. So finally the cartridge may be stopped or slowed and the interfaces between cells and plasma may be measured at each of the blood aliquots, and analysed as described above.

For completeness, it is noted that a crest of the pressure balance channels (54-57) is disposed radially inward of a maximum fill level of the sample chamber (30) (in the illustrated embodiments radially inward of the sample chamber (30)) to prevent syphoning of liquid in the chamber (30) through the pressure balance channels (54-57). As a further anti-syphoning measure, a region between the crest and the vent port can be provided with a sudden, e.g. rectangular, expansion to introduce a surface tension barrier. In such embodiments, there is greater flexibility in the positioning of the crests. Other anti-siphoning measures, such as shown in FIG. 4B can be used.

It should also be noted that the respective filling times of the aliquot chambers will not be constant as the level in the sample chamber (30) progressively drops due to the reducing liquid head. In some embodiments, the rotational frequency may be increased to counter this effect, or the aliquot chambers can be radially staggered (outwards from the first aliquot chamber (61), for example each subsequent aliquot chamber being at least partially radially outside the previous aliquot chamber in the sequence) to maintain the liquid head seen by each sequentially filled chamber roughly the same for each aliquot chamber as the sample chamber (30) empties. In alternative embodiments, the respective supply channel cross-sections can be adjusted alternatively or additionally to adjust the flow rates, e.g. to keep filling times approximately the same for all aliquot chambers.

A specific implementation of a cartridge as described with reference to FIGS. 4A-L is now discussed. The cartridge (10) consists of two disk-shape parts of 0.6 mm thickness each bonded together, having an outer diameter of 120 mm and an inner hole of 15 mm diameter centered at the rotational axis (20). The sample chamber (30) is of 0.2 mm depth engraved into the upper cartridge part (11) having an average radius of 20 mm from the rotational axis (20) and being capable of holding 20 µl of liquid. The channels (47), (48), etc have a depth of 0.05 mm and 0.1 mm width. The aliquot chambers (61), (62), (63) and (64) have depth of 0.2 mm and a volume of 5 µl each. The volume in the initial chamber (30) above the level (i.e. with a radius smaller than) of the air channel (55) is capable of holding 4.95 µl. The volume in the sample chamber (30) below (i.e. with a radius greater than) the air channel (55) and above the level (i.e. with a radius smaller than) the air channel (56) is capable of holding 5.05 µl. The volume in the sample chamber (30) below (i.e. with a radius greater than) the air channel (56) and above the level (i.e. with a radius smaller than) the air channel (57) is capable of holding 5.05 µl. The volume in the initial chamber (30) below (i.e. with a radius greater than) the air channel (57) is capable of holding 5.05 µl.

We now further describe one implementation example of a method for sequential aliqoting an using the cartridge of FIGS. 4A to 4L. The cartridge (10) is placed in the rotor (110) with the initial chamber (30), having the inlet hole (31) sealed and holding 20 µl of standard buffer PBS. Then the rotor (110) is rotated at 20 Hz. After 10 seconds the first aliquot chamber (61) is filled, while there is no flow into the other liquid aliquot chambers. When the first aliquot chamber (61) is finally filled the air channel (55) becomes open and enables air pressure balance between the initial chamber (30) and the second liquid aliquot (62). The motor (110) keeps rotating the cartridge (10) at 20 Hz and liquid flows from the initial chamber (30) into the second aliquot chamber (62). During this process no liquid flows into any other liquid aliquot chamber (63) and (64) since their respective air pressure channels (56) and (57) are closed and present air pressure balance between input chamber and output chamber. After 24 s from the start, and at the same time that the second aliquot chamber (62) becomes filled the second air pressure channel (56) becomes open and liquid starts flowing into the third liquid aliquot chamber (63). At this stage the channel (55) may contain liquid in its most radial positions. The liquid volume contained in these channels is insignificant due to their very small dimensions (depth of 0.05 mm and 0.1 mm width). After 40 s from the start, and at the same time that the third aliquot chamber (63) becomes filled the third air pressure channel (57) becomes open and liquid starts flowing into the forth liquid aliquot chamber (64). After 60 s from the start the last aliquot chamber (64) is filled and flow stops. The precise timing of each aliquot may be controlled by acting on the rotational speed of the cartridge (10). For a certain rotational speed, the filling time of each liquid aliquot increases sequentially since the liquid column initial chamber decreases.

In one other alternative embodiment of a sequential aliquoting cartridge, the sample chamber (30) is connected to multiple aliquot chambers (61, 62, 63, 64) by long and thin channels. Simultaneous filling of a certain aliquot chamber occurs together with filling the channel connecting to the next chamber. FIG. 5A Illustrates a section of a cartridge according to one embodiment of the present invention, where the initial chamber (30) is connected to multiple blood aliquot chambers by sufficiently long and thin channels, and simultaneous filling of a certain aliquot occurs with channel filling connecting to the next chamber. As with the cartridge described above, the cartridge can be used for sedimentation rate analysis for example using a device as described above with reference to FIG. 3.

FIG. 5B illustrates a first operational state of the cartridge (10), when the cartridge is rotated about the rotation axis (20) and liquid flows from the sample chamber (30) into the first aliquot chamber (61). The channel (40) connecting the sample chamber (30) with the first aliquot chamber (61) is made sufficiently small in order to minimize the blood flow rate when compared with the flow rate of blood in the channel (47) connecting into the second aliquot chamber (62). The channel (55) enables the air to escape through the chambers (62, 63, 64) and channels (56, 57, 54) from the chamber (61) while it is being filled. If the flow rate in the channel (47) is sufficiently large when compared to the filling rate of the chamber (61) then at a certain moment and while the cartridge (10) is being rotated along its axis (20), the second chamber (62) will start to be filled. It is also necessary for sedimentation rate analysis that both flow rates are sufficient slow when compared to the typical timescales of blood sedimentation, otherwise all blood aliquots would have the same characteristic cell fraction.

FIG. 5C illustrates a second operational state of the cartridge (10) previously illustrated in FIG. 5A, when the cartridge is rotated along the rotation axis (20) and liquid flows from the sample chamber (30) into the third aliquot chamber (63). By continuing the rotation of the cartridge (10) at a certain moment the initial chamber (30) will be empty and the last blood aliquot chamber (64) will be partially filled.

FIG. 5D illustrates a third, last operational state of the cartridge (10) previously illustrated in FIG. 5A, when each blood aliquot is fully sedimented and each blood aliquot in a respective aliquot chamber contain a different cell fraction.

Again, as previously detailed, each interface between cells and plasma is measured in a device illustrated in FIG. 3 and analysed as described above.

In an additional embodiment which can be combined with all of the above the processor (150) obtains a measurement of the interface between the blood plasma and air at each blood aliquot chamber, and knowing the geometry of each structure of the cartridge, determines in this way the total blood volume of the blood sample (70). The processor (150) then compares the measured blood volume of the blood sample (70) with pre-defined values for acceptance or rejection criteria. If the measured blood volume is within the acceptance range then the test (e.g. sedimentation rate measurement) may be accepted or if measured blood volume is outside the blood volume acceptance criteria, then the test is rejected.

The following is also described:

A blood analysing device comprising:
A rotatable cartridge as described above or otherwise comprising an initial blood chamber capable of holding a blood sample and multiple blood aliquot chambers placed in radially outward from the initial blood chamber;
A motor capable of rotating the cartridge about an axis to provide sequential aliquoting of the blood sample into multiple aliquot chambers and then a full sedimentation of the blood present in each blood aliquot chamber;
A light source arranged for illuminating the cartridge in the region of the aliquot structures;
An optical detector capable of measuring the interface of blood cells and blood plasma present at each blood aliquot chamber;
An Erytrocyte Sedimentation Rate processor connected to the optical detector and arranged for determining an erythrocyte sedimentation rate, ESR, in said blood sample based on the information of the position of the interface between blood cells and blood plasma at each blood aliquot chamber.

A device as described above, wherein the Erytrocyte Sedimentation Rate processor is further arranged for determining the Hematocrit fraction of the said blood sample based on the information of the position of the interface between blood cells and blood plasma at each blood aliquot chamber.

A device as described above, wherein the series of multiple blood aliquot chambers in the cartridge are connected to the initial blood chamber by liquid channels and also by air pressure channels, and each air pressure channel is normally closed preventing air pressure equilibrium while the previous blood aliquot is being filled and become open after filling the previous blood aliquot.

A device as described above, wherein the series of multiple blood aliquot chambers in the cartridge are connected to the initial blood chamber by long liquid channels and each blood aliquot chamber is being filled while blood flows in the channel connecting into the next blood aliquot chamber.

A device as described above, wherein the cartridge is composed of two plastic parts and bonded together, made of polycarbonate or acrylic or any other thermoplastic material.

A device as described above, being of circular shape, having a diameter of 120 mm.

A device as described above, being of circular shape and having a thickness smaller than 2 mm.

A device as described above, wherein the chambers and channels have a thickness smaller than 0.5 mm.

A method, as described above or otherwise, of analysing a blood sample contained in a cartridge comprising the steps of:
routing the blood sample from its initial chamber into multiple blood aliquot chambers by rotating the cartridge at a certain rotational speed;
performing the full blood cell sedimentation of each blood aliquot present at each blood aliquot chamber;
stopping the cartridge and measuring the interface between blood cells and blood plasma at each blood aliquot chamber;
Determining an erythrocyte sedimentation rate in said blood sample based on said positions of each interface of blood cells and blood plasma of each blood aliquot chamber.

A method as described as, wherein the measurement of each interface of blood cells and blood plasma at each blood aliquot chamber is further used for determining the hematocrit fraction of the said blood sample.

A method as described above, wherein the cartridge is rotated at rotational frequencies greater than 10 Hz and smaller than 200 Hz.

A method as described above, wherein a further measurement between the blood plasma and air at each blood aliquot chamber enables the determination of the total blood sample volume and the processor compares the total blood volume with acceptance and rejection criteria and the measurements and accepted if the blood volume is within the acceptance range or the blood test is rejected if the blood volume is outside the blood volume acceptance criteria.

The disclosure is not limited to any specific type of cartridge dimensions or materials, nor to a specific number of blood aliquots. Furthermore, the blood aliquots may be placed at different radial positions in order to optimize the partial sedimentation effect, for example as described above.

It will be understood that the cartridges and microfluidic structures disclosed herein are not limited in their application to blood analysis but more generally enable analysis of sedimentation rates in a wide range of samples. They further are not limited to sedimentation rate applications but provide a sequential aliquoting mechanism of general application.

For the avoidance of doubt, the term "microfluidic" is referred to herein to mean devices having a fluidic element such as a reservoir or a channel with at least one dimension below 1 mm.

The present invention is thus not intended to be limited to the particular described embodiments and examples but is defined by the appendent claims.

The invention claimed is:

1. A device for handling liquid, the device being rotatable about an axis of rotation to drive liquid flow within the device and comprising:
a reservoir chamber configured to accept a liquid and to dispense the liquid as the device rotates about the axis;
a plurality of receiving chambers connected to the reservoir chamber to receive liquid from the reservoir chamber as the devices rotates about the axis; and
a plurality of fluid conduits connecting the plurality of receiving chambers to the reservoir chamber to enable liquid to flow from the reservoir chamber to the plurality of receiving chambers and gas to be displaced by the liquid to vent from the plurality of receiving chambers, wherein the plurality of fluid conduits comprise a plurality of supply conduits each connected to a respective one of the plurality of receiving chambers to deliver liquid and a plurality of vent conduits each connected to a respective one of the plurality of receiving chambers to allow gas to escape, and
wherein the one or more fluid conduits are configured to begin filling each one of the plurality of receiving chambers at a different respective time while the device rotates at a substantially constant rate of rotation; and
wherein each vent conduit is connected to a respective vent port of a plurality of vent ports of the reservoir chamber to allow gas to escape into the reservoir chamber, the plurality of vent ports being mutually radially spaced along the reservoir chamber, thereby preventing liquid flow into each receiving chamber while the respective vent port is radially outward of a liquid level in the reservoir chamber and at least one other one of the plurality of vent ports is radially inward of the liquid level in the reservoir chamber.

2. A device as claimed in claim 1, wherein the reservoir chamber is configured to provide a gas filled space radially inward of a maximum fill level of the reservoir chamber as the device is rotated and a first one of the vent ports is disposed radially inward of the maximum fill level.

3. A device as claimed in claim 1, wherein a first one of the plurality of vent ports is disposed at a radially innermost aspect of the reservoir chamber.

4. A device as claimed in claim 1, wherein each supply conduit is connected to a different supply port of a supply manifold conduit.

5. A device as claimed in claim 4, wherein the vent conduit of a previous receiving chamber is connected to vent the previous chamber through a subsequent chamber subsequent to the previous chamber, the supply conduit of the subsequent chamber, or both.

6. A device as claimed in claim 5, wherein the vent conduit of the previous chamber is connected to the supply circuit of the subsequent chamber.

7. A device as claimed in claim 4, wherein the supply manifold conduit comprises a meandering portion, preferably extending from a first to a last one of the supply ports.

8. A device as claimed in claim 1, configured as a microfluidic device.

* * * * *